US007632008B2

(12) United States Patent
Recht et al.

(10) Patent No.: US 7,632,008 B2
(45) Date of Patent: Dec. 15, 2009

(54) RANKING FRAGMENT TYPES WITH CALORIMETRY

(75) Inventors: Michael I. Recht, Mountain View, CA (US); Francisco E. Torres, San Jose, CA (US); Richard H. Bruce, Los Altos, CA (US); Alan G. Bell, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 202 days.

(21) Appl. No.: 11/760,236

(22) Filed: Jun. 8, 2007

(65) Prior Publication Data

US 2008/0304541 A1 Dec. 11, 2008

(51) Int. Cl.
*G01K 17/00* (2006.01)
(52) U.S. Cl. ....................................... 374/31
(58) Field of Classification Search .................. 374/10, 374/31, 36; 422/50, 51; 435/6
See application file for complete search history.

(56) References Cited

U.S. PATENT DOCUMENTS

| 5,312,587 | A | 5/1994 | Templer et al. |
| 5,451,371 | A | 9/1995 | Zanini-Fisher et al. |
| 5,486,337 | A | 1/1996 | Ohkawa |
| 5,813,764 | A | 9/1998 | Visser et al. |
| 5,967,659 | A | 10/1999 | Plotnikov et al. |
| 6,079,873 | A | 6/2000 | Cavicchi et al. |
| 6,096,559 | A | 8/2000 | Thundat et al. |
| 6,193,413 | B1 | 2/2001 | Lieberman |
| 6,331,074 | B1 | 12/2001 | Kimura |
| 6,380,605 | B1 | 4/2002 | Verhaegen |
| 6,436,346 | B1 | 8/2002 | Doktycz et al. |
| 6,545,334 | B2 | 4/2003 | Verhaegen |
| 6,648,503 | B2 | 11/2003 | Tanaka et al. |

(Continued)

FOREIGN PATENT DOCUMENTS

WO WO 99/54730 A1 10/1999

(Continued)

OTHER PUBLICATIONS

Office communication in U.S. Appl. No. 10/303,500, mailed Jul. 23, 2007, 7 pages, published in PAIR.

(Continued)

*Primary Examiner*—Andre J Allen
(74) *Attorney, Agent, or Firm*—Leading-Edge Law Group, PLC; James T. Beran

(57) ABSTRACT

Test and reference groups of samples can be provided and concurrently combined and output signals can be provided. Each sample can have a volume not exceeding approximately 100 microliters, and each group can be provided in a region, such as in a cell of an array calorimeter. Each test group can include at least one fragment sample and one target sample, and its reference group can include similar samples. The output signals can include information about heat of reaction due to combining the fragment and target samples. For each target type, the output signals can be used to rank fragment types. For example, a subset of fragment types that react with the target type can be identified; an equilibrium constant or ligand efficiency can be obtained for each such fragment type; or a rank ordering can be obtained of such fragment types.

32 Claims, 9 Drawing Sheets

U.S. PATENT DOCUMENTS

| | | | |
|---|---|---|---|
| 6,649,343 | B1 | 11/2003 | Takeuchi et al. |
| 6,843,596 | B2 * | 1/2005 | Verhaegen .................. 374/10 |
| 6,988,826 | B2 | 1/2006 | Zribi et al. |
| 7,141,210 | B2 | 11/2006 | Bell et al. |
| 7,147,763 | B2 | 12/2006 | Elrod et al. |
| 7,416,897 | B2 | 8/2008 | Bruce et al. |
| 7,419,835 | B2 | 9/2008 | Torres et al. |
| 7,473,030 | B2 | 1/2009 | Bruce et al. |
| 7,473,031 | B2 | 1/2009 | Wolkin et al. |
| 7,521,253 | B2 | 4/2009 | Bruce et al. |
| 2002/0003830 | A1 | 1/2002 | Tanaka et al. |
| 2002/0021740 | A1 | 2/2002 | Danley |
| 2003/0016725 | A1 | 1/2003 | Whateley et al. |
| 2003/0044800 | A1 | 3/2003 | Connelly et al. |
| 2003/0152128 | A1 | 8/2003 | Verhaegen |
| 2003/0186454 | A1 | 10/2003 | Bruce et al. |
| 2003/0186455 | A1 | 10/2003 | Bruce et al. |
| 2004/0038227 | A1 | 2/2004 | Verwaerde et al. |
| 2004/0038228 | A1 | 2/2004 | Verhaegen |
| 2005/0238080 | A1 | 10/2005 | Wolkin et al. |
| 2005/0254552 | A1 | 11/2005 | Bruce et al. |
| 2005/0254994 | A1 | 11/2005 | Bell et al. |
| 2005/0265898 | A1 | 12/2005 | Bell et al. |
| 2006/0078999 | A1 | 4/2006 | Bell et al. |
| 2006/0132542 | A1 | 6/2006 | Bruyker et al. |
| 2006/0159585 | A1 | 7/2006 | Torres et al. |

FOREIGN PATENT DOCUMENTS

| | | | |
|---|---|---|---|
| WO | WO 01/85978 A2 | 11/2001 | |

OTHER PUBLICATIONS

Amendment After Final Rejection in U.S. Appl. No. 10/303,500, dated Sep. 21, 2007, 9 pages, published in PAIR.

Amendment with Request for Continued Examination in U.S. Appl. No. 10/303,500, dated Oct. 22, 2007, 13 pages, published in PAIR.

Office communication in U.S. Appl. No. 10/303,500, mailed Dec. 27, 2007, 9 pAGES, published in PAIR.

Amendment with Information Disclosure in U.S. Appl. No. 10/303,500, dated Mar. 26, 2008, 13 pages, published in PAIR.

Office communication in U.S. Appl. No. 10/303,500, mailed Jun. 30, 2008, 9 pages, published in PAIR.

Office communication in U.S. Appl. No. 11/149,632, mailed Jun. 10, 2008, 12 pages, published in PAIR.

Shuker, S.B., Hajduk, P.J., Meadows, R.P., and Fesik, S.W., "Discovering High Affinity Ligands for Proteins: SAR by NMR," Science, vol. 274, Nov. 29, 1996, pp. 1531-1534.

Fominaya, F., Fournier, T., Gandit, P., and Chaussy, J., "Nanocalorimeter for high resolution measurements of low temperature heat capacities of thin films and single crystals", Review of Scientific Instruments, vol. 68, No. 11, Nov. 1997, pp. 4191-4195.

Pierce, M.M., Raman, C.S., Nall-B.T., "Isothermal Titration Calorimetry of Protein-Protein Interactions", Methods, vol. 19, 1999, pp. 213-221.

Johannessen, E.A., Weaver, J.M.R., Cobbold, P.H., and Cooper, J.M., "A Suspended Membrane Nanocalorimeter for Ultralow vol. Bioanalysis", IEEE Transactions on Nanobioscience, vol. 1, No. 1, Mar. 2002, pp. 29-36.

Johannessen, E.A., Weaver, J.M.R., Cobbold, P.H., and Cooper, J.M., "Heat conduction nanocalorimeter for pl-scale single cell measurements", Applied Physics Letters, vol. 80, No. 11, Mar. 18, 2002, pp. 2029-2031.

Torres, F.E., Kuhn, P., De Bruyker, D., Bell, A.G., Wolkin, M.V., Peeters, E., Williamson, J.R., Anderson, G.B., Schmitz, G.P., Recht, M.I., Schweizer, S., Scott, L.G., Ho, J.H., Elrod, S.A., Schultz, P.G., Lerner, R.A., and Bruce, R.H., "Enthalpy arrays," PNAS, vol. 101, No. 26, Jun. 29, 2004, pp. 9517-9522.

Carr, R.A.E., Congreve, M., Murray, C.W., and Rees, D.C., "Fragment-based lead discovery: leads by design," DDT, vol. 10, No. 14, Jul. 2005, pp. 987-992.

Vivactis Nano Calorimetric Screening Slides presented Sep. 14, 2005, 21 pages.

Vivactis MiDiCal Poster and Single Well Nano-calorimetric Poster presented Sep. 14, 2005, 2 pages.

Vivactis N.V., "Vivactis engages into collaboration with Silicos", press release dated Apr. 27, 2006, 1 page.

Sem, D.S., "NMR-guided Fragment Assembly," M. Jahnke, W., and Erlanson, D.A., Eds., Fragment-based Approaches in Drug Discovery, 2006, pp. 149-180.

Davies, T.G., Van Montfort, R.L.M., Williams, G., and Jhoti, H., "Pyramid: An Integrated Platform for Fragment-based Drug Discovery", M. Jahnke, W., and Erlanson, D.A., Eds.,Fragment-based Approaches in Drug Discovery, 2006, pp. 193-214.

Vivactis Microplate Differential Calorimetry, printed from vvvwv.vivactis.be on Jun. 7, 2007, 2 pages.

MicroCal, LLC, "Ultrasensitive Calorimetry for the Life Sciences", printed from www.microcal.com on Jun. 7, 2007, 13 pages.

Amendment With Information Disclosure in U.S. Appl. No. 10/303,500, submitted Sep. 30, 2008, 17 pages, published in PAIR.

Notice of Allowance and Fee(s) Due in U.S. Appl. No. 10/303,500, mailed Dec. 23, 2008, 8 pages, published in PAIR.

Amendment in U.S. Appl. No. 11/149,632, submitted Sep. 5, 2008, 23 pages published in PAIR.

Office communication in U.S. Appl. No. 11/149,632, mailed Dec. 8, 2008, 14 pages, published in PAIR.

Request for Reconsideration with Information Dislosure in U.S. Appl. No. 11/149,632, submitted Jan. 6, 2009, 7 pages, published in PAIR.

Office communication in U.S. Appl. No. 11/149,632, mailed Jan. 27, 2009, 10 pages, published in PAIR.

Amendment After Final Rejection in U.S. Appl. No. 11/149,632, submitted Mar. 19, 2009, 25 pages, published in PAIR.

Office communication in U.S. Appl. No. 11/149,632, mailed Apr. 6, 2009, 3 pages, published in PAIR.

Amendment With Request for Continued Examination in U.S. Appl. No. 11/149,632, submitted Apr. 27, 2009, 19 pages, published in PAIR.

* cited by examiner ns in using calorimetry to rank fragment types that react
RANKING FRAGMENT TYPES WITH CALORIMETRY This invention was made with Government support under contract HHSN266200400058C/NO1-AI-40058 awarded by the National Institutes of Health. The Government has certain rights in the invention.

CROSS-REFERENCES TO RELATED APPLICATIONS

This application is related to the following co-pending applications, each of which is hereby incorporated by reference in its entirety: "Apparatus and method for lead profiling assay", U.S. patent application Ser. No. 10/303,446, published as U.S. Patent Application Pub. No. 2003/0186454; "Apparatus and method for multiple target assay for drug discovery", U.S. patent application Ser. No. 10/303,500, published as U.S. Patent Application Pub. No. 2003/00186455; "Apparatus and method for improved electrostatic drop merging and mixing", U.S. patent application Ser. No. 11/018,757, published as U.S. Patent Application Pub. No. 2006/0132542; "Apparatus and Method for a Nanocalorimeter for Detecting Chemical Reactions", U.S. patent application Ser. No. 11/149,632, published as U.S. Patent Application Pub. No. 2006/0078999; "Thermal Sensing with Bridge Circuitry", U.S. patent application Ser. No. 11/167,612, published as U.S. Patent Application Pub. No. 2005/0254994; "Thermal Sensing", U.S. patent application Ser. No. 11/167,635, published as U.S. Patent Application Pub. No. 2005/0265898; "Thermal Sensing", U.S. patent application Ser. No. 11/167,746, published as U.S. Patent Application Pub. No. 2005/0254552; "Resistive Thermal Sensing", U.S. patent application Ser. No. 11/167,748, published as U.S. Patent Application Pub. No. 2005/0238080; "Producing Layered Structures Using Printing", U.S. patent application Ser. No. 11/318,926; "Passive Electronic Devices", U.S. patent application Ser. No. 11/318,967; and "Layered Structures on Thin Substrates", U.S. patent application Ser. No. 11/318,975.

BACKGROUND OF THE INVENTION

The present invention relates generally to techniques that obtain information about combinations of ligands and targets, such as by calorimetry. The term "calorimetry" is used herein to refer to any measurement of absorbed or evolved heat or specific heat or the like; a measurement by calorimetry may be referred to as a "calorimetric measurement". A machine, device, or other apparatus that can be used in calorimetry may be referred to as a "calorimeter".

U.S. Pat. No. 7,141,210, incorporated herein by reference, describes a nanocalorimeter array for detecting chemical reactions. The array includes at least one thermal isolation region with a thermal measurement device connected to detection electronics. U.S. Patent Application Publication Nos. 2003/0186454 and 2003/0186455 describe assay techniques for drug discovery using such an array.

It would be advantageous to have improved techniques to obtain information about combinations of ligands and targets.

SUMMARY OF THE INVENTION

The invention provides various exemplary embodiments, including methods and systems. In general, the embodiments involve use of calorimeters or calorimetry to rank fragment types that react with a target type.

These and other features and advantages of exemplary embodiments of the invention are described below with reference to the accompanying drawings.

DETAILED DESCRIPTION

Figure 1:
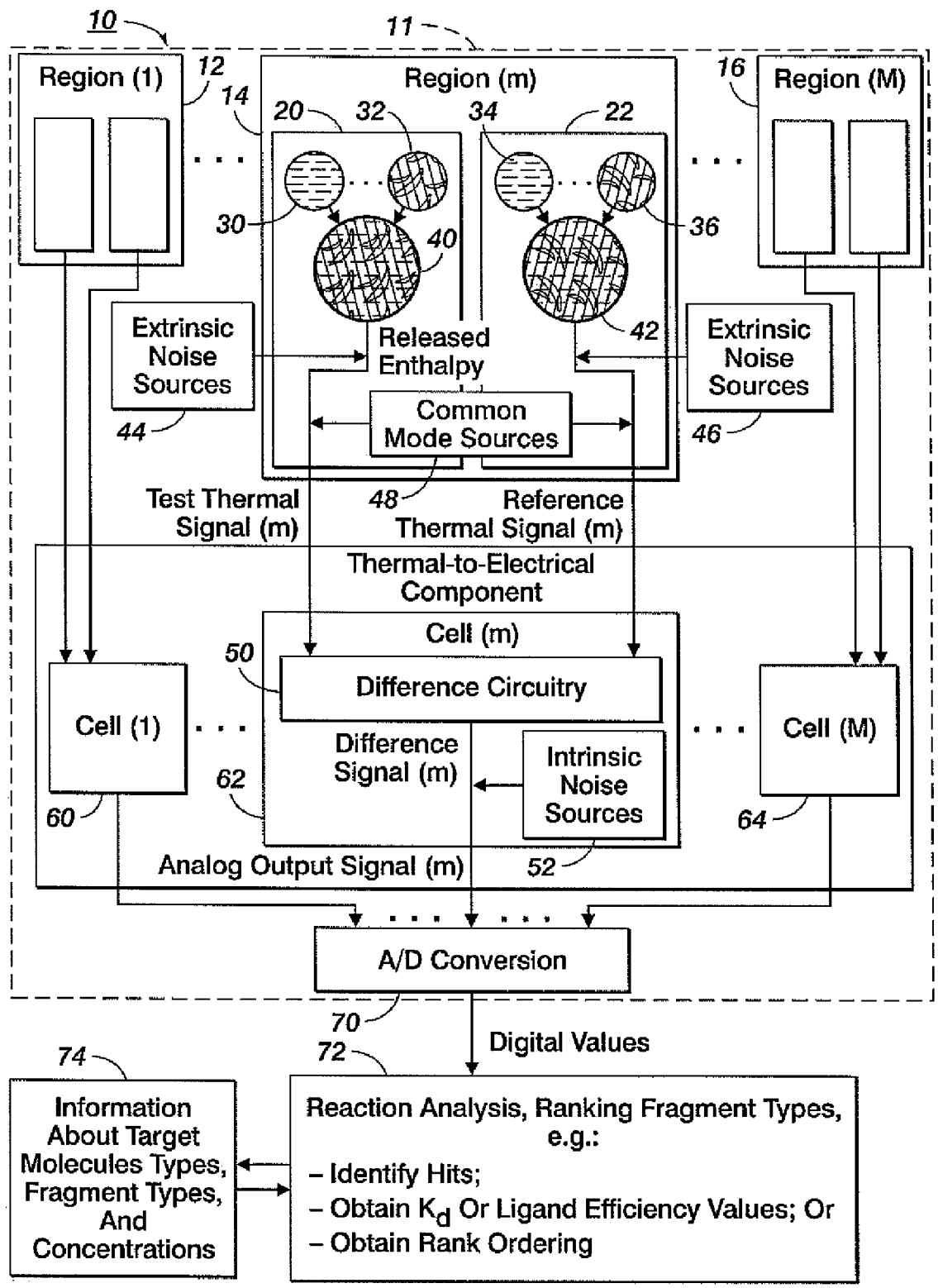
FIG. 1 is a schematic flow diagram showing general operations in using calorimetry to rank fragment types that react with target types.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

The term "target molecule," or simply "target," refers to a compound, such as a biological compound, whose activity it is desirable to affect. For example, a target molecule may participate in a known biological pathway or be involved in a biological regulation function, and it may be desirable to find other compounds that can affect the target molecule's biological activity. For that purpose, it is desirable to find other compounds that react chemically with the target molecule, and are therefore candidates for affecting its biological activity, possibly candidates for therapeutic agents. If a target molecule is a peptide, protein, protein complex, nucleic acid, protein-nucleic acid complex such as a ribo- or deoxyribonucleoprotein, or another such molecule with at least one chain of amino acids or nucleotides, such as a peptide, protein, or nucleic acid known or believed to be involved in the etiology of a disease, condition, or pathophysiological state, or in the regulation of a physiological function, it may be referred to herein as a "target protein/nucleic acid."

The term "ligand" is used herein to refer to an agent that binds to a target molecule. A ligand can be any compound, molecule, or complex, including, without limitation, metals, peptides, proteins, lipids, polysaccharides, nucleic acids, small organic molecules, combinations of the above, and so forth. For a target protein/nucleic acid, a ligand may bind the target protein/nucleic acid in its native conformation, or when it is partially or totally unfolded or denatured. The term "ligand" is not used herein in the limited sense of an agent that binds a recognized functional region of a target protein/nucleic acid, but could be an agent that binds any surface or internal sequence or conformational domain of a target protein/nucleic acid, including an agent that, in and of itself, has no apparent biological function other than its ability to bind the target protein/nucleic acid in one of these ways.

An operation that searches through various possible agents, sometimes referred to herein as "test ligands," for their ability to bind to a set of one or more target molecules is referred to as "screening." In a typical approach to screening, target molecules are brought together with test ligands in such a way that binding would occur if any of the test ligands is in fact a ligand for one of the target molecules; the term "sample" is used herein to refer to any drop, droplet, or other distinct object that contains one or both of target molecules and agents being tested for binding. For example, a sample could include both test molecules and ligands, and temperature could be measured with a calorimeter to determine whether binding occurs. If sufficient binding occurs to meet an appropriate threshold criterion, the binding event is referred to herein as a "reaction"; if the criterion depends on measurement of a result or other characteristic of the binding event, the ligand and target could be said to "react measurably" or, more simply, to "react." In general, a reaction is accompanied by a release of energy in the form of heat or by the absorption of energy in the form of heat, and the quantity of energy released or absorbed is referred to herein as "heat of reaction" or "enthalpy." Heat of reaction, however, is but one type of information that can be obtained by measuring or otherwise observing reactions between ligands and target molecules, and all such types of information are referred to collectively herein as "ligand-target information." It is well known, for example, to obtain an equilibrium constant such as $K_d$ for a given combination of a ligand and a target molecule, and such a value can in turn be used to obtain a value for ligand efficiency using known relationships, as described below.

Various techniques have been developed for obtaining ligand-target information. Some such techniques test agents sufficiently small that they are not themselves suitable as drugs but could be included in more complex drug-sized compounds; such test ligands are referred to herein as "fragments". Techniques that test fragments to determine whether they are suitable for inclusion in such a compound are typically referred to as "fragment-based screening" or "FBS." Some known FBS techniques test fragments with molecular weights of approximately 150-250 Da, but FBS can also be performed with fragments of appropriate sizes larger or smaller than this range. FBS techniques that use x-ray crystallography, nuclear magnetic resonance (NMR), and other such techniques are described in Carr, R. A. E., Congreve, M., Murray, C. W., and Rees, D. C., "Fragment-based lead discovery: leads by design," Drug Discovery Today, Vol. 10, No. 14, July 2005, pp. 987-992.

The exemplary implementations described below address problems that arise with FBS techniques using X-ray crystallography techniques, NMR techniques, and other similar techniques. Among the problems are the difficulties of obtaining ligand-target information, the use of large amounts of material, and the long time necessary to obtain FBS results with previous techniques.

In one X-ray crystallography approach to FBS, cocktails containing four to ten fragment compounds are soaked into crystals of a protein of interest. Using automated X-ray data collection and data processing, the density of the bound ligands is identified. Although several leads have been identified using this technique, the technique has some limitations; for example, current X-ray crystallography techniques cannot determine affinity of a ligand, and affinities or inhibition constants must therefore be separately determined using standard bioassays.

In a ligand-based NMR approach to FBS, a relatively low target concentration such as 10-20 µM and an excess of ligand such as 10-20 fold are mixed; examples of this technique include saturation transfer difference (STD) or the Water-LOGSY technique. Ligand-based techniques allow screening of pools of compounds and identification of a hit from the pool. They can also be used to detect a tight-binding ligand by using it to displace a weaker binding ligand, because this results in a reduction of the NMR signal from the weaker binding ligand. Also, NMR techniques can be used to determine $K_d$ for a weak-binding ligand by a direct STD-based titration.

In a protein-based NMR approach to FBS, structural information for proper placement of fragments in a protein binding site can be obtained if full chemical shift assignments for the protein are available and structure has been calculated. In these techniques, a ligand's $K_d$ can be determined by quantitatively monitoring chemical shift changes in a titration experiment. In general, however, protein-based techniques consume more protein than ligand-based techniques, and they also require isotopically labeled protein, which is not possible for all proteins of interest. Furthermore, size limitations in NMR techniques might require selective labeling of amino acids at methyl groups and may preclude full chemical shift assignments.

An example of NMR techniques that have shown promise is a technique called "SAR by NMR." The SAR by NMR technique assumes that linking of two fragments that can simultaneously bind with moderate affinity to proximal sites on a target protein/nucleic acid will yield a high-affinity ligand.

In general, however, NMR techniques require a large amount of protein and a long time; for example, it has been estimated that a ligand-based 10,000 compound screen with 10 compounds per pooled sample would take three months and use 50 mg of protein.

The exemplary implementations described below involve calorimetry, which, as mentioned above, can measure quantity of absorbed or evolved heat or specific heat. For example, the exemplary implementations perform calorimetry to rank types of fragments that react with types of targets. As used herein, an operation "ranks" types of fragments if the operation produces information that distinguishes between the types, such as by identifying a subset of types that meet a criterion; by providing a constant or other value for each type; or by listing a number of types in a ranked order.

The exemplary implementations described below further involve use of calorimeters or calorimetric components. In general, a calorimeter may be used by a human operator, or it may be included in a system in which it is operated automatically or partially automatically. As used herein, the term "system" refers to a combination of two or more parts or components that can perform an operation together. A system may be characterized by its operation; for example, a "fragment ranking system" is a system that operates somehow to rank types of fragments.

Within a system, device, or other article, components and parts may be referred to in a similar manner. One component of a calorimeter, for example, can be described as a "thermal-to-electrical component," meaning that the component receives or otherwise obtains thermal signals and, in response, obtains electrical signals that include information from or about the thermal signals; similarly, the term "processing component" can refer to a component that performs data processing operations. In addition, a component or part may be identified by characteristics other than its operation.

The terms "thermal signal" and "thermally conductive" or "thermally conducting," as used herein, are related. A component, layer, or other structure is "thermally conductive" or "thermally conducting" if it sufficiently conducts "thermal signals" from one position or region to another that concurrent operations in the other position or region can be affected by the thermal signals.

The term "sensing" is used herein in the most generic sense of obtaining information from a physical stimulus; sensing therefore includes actions such as detecting, measuring, and so forth. "Thermal sensing" is sensing of a thermal stimulus such as heat, temperature, or random kinetic energy of molecules, atoms, or smaller components of matter. A "thermal sensor" is accordingly an electronic device that performs thermal sensing. More specifically, if thermal signals include information, a thermal sensor that receives the thermal signals may be able to sense the information.

The term "electrical signal" is used herein to encompass any signal that transfers information from one position or region to another in an electrical, electronic, electromagnetic, or magnetic form. Similarly to thermal signals, electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage. The generic term "signal" is used herein to encompass not only thermal signals and electrical signals but also other types of signals, e.g. mechanical signals. The terms "calorimeter" and "calorimetry" are broad enough to encompass devices, articles, and operations that provide analog or digital electrical output signals or both or other types of output signals, and it is foreseeable that calorimeters with new types of output signals will be developed in the future.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

In the implementations described herein, systems or parts or components of systems may sometimes be referred to as "attached" to each other or to other systems, parts, or components or visa versa, and operations are performed that "attach" systems or parts or components of systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also integrally forming components or parts and making other types of connections such as electrical connections between or among devices or components of circuitry or thermal connections between or among thermal components. A combination of one or more parts connected in any way is sometimes referred to herein as a "structure".

Some of the components described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

An "integrated structure" is a structure with electrical components and connections produced by microfabrication or similar processes. An integrated structure may, for example, be on or over a substrate on which it was produced or another suitable support structure. Other components could be on the same support structure with an integrated structure, such as discrete components produced by other types of processes.

Implementations of integrated structures described herein include features characterized as "cells" and "arrays", terms that are used with related meanings: An "array" is an arrangement of "cells". In general, each cell of an array includes a bounded area or region, and the bounded area or region contains parts or components of an integrated structure by or with which an operation can be performed separately from other cells. Although each cell of an array could in principle be unique, a typical array includes cells that are at least similar and, in some cases, substantially identical.

An "array calorimeter" is an array that includes cells that can be operated to perform calorimetry. In exemplary implementations described below, each cell of an array calorimeter can include two regions, and test samples can be combined in one region while reference samples are combined in another. Array calorimeters could be implemented in various other ways, some of which are suggested below.

In general, some of the structures, elements, and components described herein are supported on a "support layer" or "central layer", which terms are used herein to mean a layered structure that can support other structures; a surface of such a layer that supports another structure may be referred to as a "support surface". More specifically, a support layer or central layer could be a "substrate", used herein to mean a layer or layered structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a substrate or other layer or layered structure with a support surface may have any appropriate orientation.

FIG. 1 illustrates general operations in an exemplary implementation that uses calorimetry to rank fragment types that react with target types, sometimes referred to herein as "ranking fragment types"; a combination of a fragment type and a target type is sometimes referred to herein as a "fragment-target combination". The illustrated implementation uses calorimeter 10, within which thermal-to-electrical component 11 receives thermal signals from an array of M regions, of which region (1), region (m), and region (M) are illustrated by boxes 12, 14, and 16, respectively. Inside box 14 are additional details that could be present in all regions of the array or in a subset of the regions. As suggested by the dashed line around boxes 12, 14, and 16 in FIG. 1, the array of regions could be in, on, or otherwise thermally connected with calorimeter 10, depending on the details of implementation.

As shown in box 14, region (m) includes two areas 20 and 22, with area 20 illustratively providing a test thermal signal and with area 22 illustratively providing a reference thermal signal, although in general either area could be used to provide either type of thermal signal. For this purpose, however, a group of samples in area 20 includes target sample 30 and fragment sample 32. In general, an operation "provides" groups of samples if the operation somehow makes the samples available for subsequent operations; if the samples are, for example, drops or droplets, they could be provided in various ways, including drawing fluid from a reservoir of some sort to produce drops or droplets or transferring drops or droplets to positions in which they are available for subsequent operations.

Target sample 30 includes target molecules of one or more types, referred to herein as "target types"; molecules of each target type all have approximately the same chemical structure (such as a protein's amino acid sequence, a nucleic acid's nucleotide sequence, and so forth), meaning that their chemical structures are sufficiently similar that they react with substantially the same set of ligands. Similarly, fragment sample 32 includes fragments of one or more types, referred to herein as "fragment types"; fragments of each fragment type all have approximately the same chemical structure, meaning that their chemical structures are sufficiently similar that they react with substantially the same set of targets. In performing FBS, it can be especially beneficial to use fragment types with chemical structures that are internally diverse, so that they have potential to interact with different types of target types, such as a variety of target protein/nucleic acids or other targets. In addition, fragment samples in different regions can have different concentrations of fragments of a given fragment type. A number of fragment samples are described herein as having "different concentrations" for a given fragment type if any two of the fragment samples have different concentrations—it is possible that more than one of the fragment samples will have the same concentration but that one or more other fragment samples will have a different concentration.

In exemplary implementations, each sample in the group in area 20 can be very small, such as not exceeding approximately 100 microliters; small samples provided as drops of solution are sometimes referred to herein as "droplets", and droplets could have various sizes, such as 100 microliters, 10 microliters, 1 microliter, 500 nanoliters, 250 nanoliters, and so forth. Various constraints can affect the choice of droplet size, including a need to have a large enough volume so that exiting heat is small compared to heat generated, a need to have a small enough volume to be deposited or injected in the small area or region of a cell and large enough so that the heat capacity of the volume is large compared to the heat capacity of the detector. In current implementations as described below, droplets of approximately 250 nanoliters have been successfully used, and it is foreseeable that somewhat smaller samples will be used as technology advances. Furthermore, in current implementations, two droplets of approximately equal size are merged, one a target sample and the other a fragment sample, a technique that is one example of "combining" groups of samples, a generic expression used herein to refer to any technique that causes separate samples to become a single combined sample.

A technique that combines droplets of approximately equal size avoids concentration issues and solvent matching issues that would arise if a small sample of one type were merged into a large reservoir-like sample of the other type. Also, much less material is necessary to obtain a thermal signal than would be necessary if one or more of the samples are significantly larger. The resulting thermal signals are sometimes also referred to as "heats" because they include information about heat of reaction.

Area 22 also includes a group of samples, with samples 34 and 36 being similar, respectively, to samples 30 and 32 in area 20, and with other samples in the two groups also being similar. Groups of one or more samples are described herein as "similar" if each group includes the same number of samples and each sample in each group is similar in volume (and possibly other ways) to a counterpart sample in each of the other groups; for example, a reference sample may be similar to a test sample that includes a target type or a fragment type if it is similar in, e.g. volume, density, viscosity, and other respects but does not include molecules of the target type or fragments of the fragment type.

In operation, the two groups of samples in areas 20 and 22 can be concurrently combined, resulting in merged sample 40 in area 20 and merged sample 42 in area 22. The group of samples in area 22, however, includes reference samples that do not react when combined, so that no reaction occurs in merged sample 42. The samples in the group in area 20, on the other hand, may react when combined, so that a reaction may occur in merged sample 40; more specifically, fragments from sample 32 may react with or in the presence of target molecules in target sample 30, and such a reaction may release enthalpy. Reaction may occur in merged sample 40 as the merged samples mix or as their constituents diffuse within merged sample 40.

The thermal signal from merged sample 40, in addition to information about released enthalpy and common mode thermal events as described below, also includes noise from extrinsic noise sources 44, examples of which are discussed in greater detail below. Similarly, the reference thermal signal can include noise from extrinsic noise sources 46 such as violations of common mode, as mentioned below.

In a current implementation, the two groups of samples are combined "concurrently," meaning that they combine to form merged samples 40 and 42 at the same time; as a result, the test and reference thermal signals are subject to some of the same extraneous thermal effects. More generally, groups of samples are "combined in parallel" if there is any overlap between times during which the groups are present, before or after being combined; for example, groups of samples in regions 12, 14, and 16 could be deposited and then combined in parallel, with the test and reference groups in each region being combined concurrently.

As used herein, the term "extrinsic noise" does not, however, include thermal signal components from both merged samples 40 and 42 that are equal, represented in FIG. 1 as contributed by common mode sources 48; examples of contributions by common mode sources 48 could include heat of dilution or other transient or steady-state thermal effects that are the same for both merged samples. Therefore, thermal-to-electrical component 11 includes difference circuitry 50, which could, for example, be implemented with a Wheatstone bridge and other components as described in greater detail below. Difference circuitry 50 receives both thermal signals from areas 20 and 22 and provides a difference signal that includes information about enthalpy released in merged sample 40, but in which the contributions from common mode sources 48 are cancelled in obtaining the difference signal. On the other hand, the difference signal includes noise from extrinsic noise sources 44 and 46 and also from intrinsic noise sources 52, sources that exist within component 11, examples of which are described in greater detail below; in implementations with thermal sensors that provide voltage signals as output, for example, intrinsic noise sources 52 can include sources that cause voltage fluctuations in the output signals. In general, the term "difference signal" refers herein to any signal that indicates a difference between two other signals; a difference signal need not be obtained by an actual subtraction operation or the like, but can be obtained by any combination of components and/or operations that produces a signal indicating difference.

In accordance with the above description, the generic term "noise", as used herein, does not include thermal signal components accurately indicating enthalpy released by reactions, nor does it include thermal signal components that result from common mode sources that equally affect both test and reference thermal signals and can therefore be removed by difference circuitry 50. Noise can, however, include various types of extrinsic noise such as thermal signal noise due to mixing and diffusion slower than the characteristic time for thermal dissipation from the detector or due to differences between test and reference sample volumes, sample shapes, sample temperatures, sample placements, reagent mixing, reagent diffusion, sample evaporation, convective or conductive heat transfer, or other violations of common mode; in general, most extrinsic noise can be characterized as thermal noise. Noise can also include various types of intrinsic noise, such as noise arising in thermal sensors, noise arising in amplifiers or other difference circuitry components, noise arising in analog-to-digital conversion, and so forth; in general, most intrinsic noise can similarly be characterized as electronic noise.

In exemplary implementations, output digital signals can be obtained in which the major noise components arise either from extrinsic noise sources 44 and 46 or from intrinsic sources 52 as described above; furthermore, an analog output signal from a cell can have very low noise from extrinsic and intrinsic noise sources, such as approximately 1.0 J/L or less. Results with a current implementation indicate that intrinsic noise can be reduced to 0.05 J/L, while extrinsic noise is significantly higher. Also, although the contribution from intrinsic noise sources may already be reduced almost to the practical limit, the contribution from extrinsic noise sources could foreseeably be significantly reduced as technology advances. As a result, the analog output signal can be very sensitive, making it possible to use smaller concentrations as described above. In current implementations, noise has been sufficiently reduced that measurements of temperatures of reaction in the range of 10 $\mu°$ C. have been obtained.

As suggested by boxes 60, 62, and 64, thermal-to-electrical component 11 can be implemented with an array of cells, each of which includes an implementation of difference circuitry 50 for a respective one of the regions; in this implementation, calorimeter 10 is an example of an array calorimeter as defined above. If implemented in this manner, the output from component 11 can include an analog output signal from each cell, with the analog output signal from cell (m) being the difference signal described above.

The analog output signals from component 11 could be processed in a wide variety of ways to obtain various types of information. As illustrated in FIG. 1, an initial operation can convert analog output signals to digital values, as shown in box 70. This operation could be performed in any of a variety of ways; for example, analog-to-digital (A/D) conversion could be performed completely in parallel for all cells in component 11, completely serially for one cell at a time, or with any appropriate combination of serial and parallel operations. More generally, the operation in box 70 provides digital values indicating information about heats of reaction. Any or all of the analog output signals or the digital values or other types of signals could be considered as "output signals"; in general, an operation "provides" output signals if it makes the output signals available for subsequent operations.

As suggested by the dashed line around box 70 in FIG. 1, circuitry that performs the operation in box 70 could be a part of calorimeter 10 or could alternatively be included in a separate component connected to receive analog output signals from calorimeter 10, depending on the details of implementation; furthermore, circuitry implementing one or more of the other components in FIG. 1, e.g. boxes 72 and 74, could also be included in calorimeter 10.

In an exemplary implementation, reaction analysis, shown in box 72, can employ digital values from box 70 to rank fragment types. A reaction analysis operation can access various other types of data, including information about target molecule types, fragment types, and concentrations in samples in each region, as shown in box 74. In general, an operation "uses" output signals such as the digital values or other signals or data if the result of the operation depends on the signals or data.

Reaction analysis in box 72 can be performed in various ways. In initial screening, for example, reaction analysis in box 72 could include operations that identify fragment types that react measurably with a given target type according to an appropriate criterion; such fragment types are sometimes referred to herein as "hits". In titration-based screening, on the other hand, reaction analysis in box 72 can include calculations that determine the effect of fragment concentration on released enthalpy; more specifically, enthalpy released can be analyzed as a function of fragment concentration to obtain, for example, an equilibrium constant $K_d$ or a ligand efficiency for each fragment type that reacts measurably with a given target type or to obtain a rank ordering of a number of such fragment types, such as by ligand efficiency or binding strength. Other calculations could be performed to rank fragment types in other ways.

Because the digital values from box 70 include both signal components with information about heats of reaction and also noise components indicating intrinsic and extrinsic noise as described above, reaction analysis in box 72 can also include operations to extract a signal component from digital values, an operation sometimes referred to herein as "deconvolution." With a low signal-to-noise ratio, deconvolution of this type can be very important in determining fragment-target combinations that resulted in reactions and, if so, the magnitude of heats of reaction. In applications where a large number of fragment-target combinations are being considered, the computation necessary for this type of deconvolution can be extraordinarily time consuming; as described in greater detail below, however, techniques can be developed to accomplish deconvolution in a shorter time, and time can further be reduced by increasing parallelism where possible, such as during measurement or by multiplexing fragment types and target types when appropriate.

The general operations shown in FIG. 1 could be implemented in many different ways using a wide variety of calorimeters. FIGS. 2-10 illustrate features of an exemplary implementation employing a nanocalorimeter similar to implementations described in U.S. Patent Application Publication Nos. 2005/0238080, 2005/0254552, 2005/0254994, and 2005/0265898, all incorporated herein by reference in their entireties. The operations illustrated in FIG. 1 could, however, be implemented using other types of calorimeters, including devices in which samples other than drops are combined, devices in which a difference between thermal signals is not obtained, devices with a single region in which reactions can occur rather than an array, and so forth.

Figure 2:
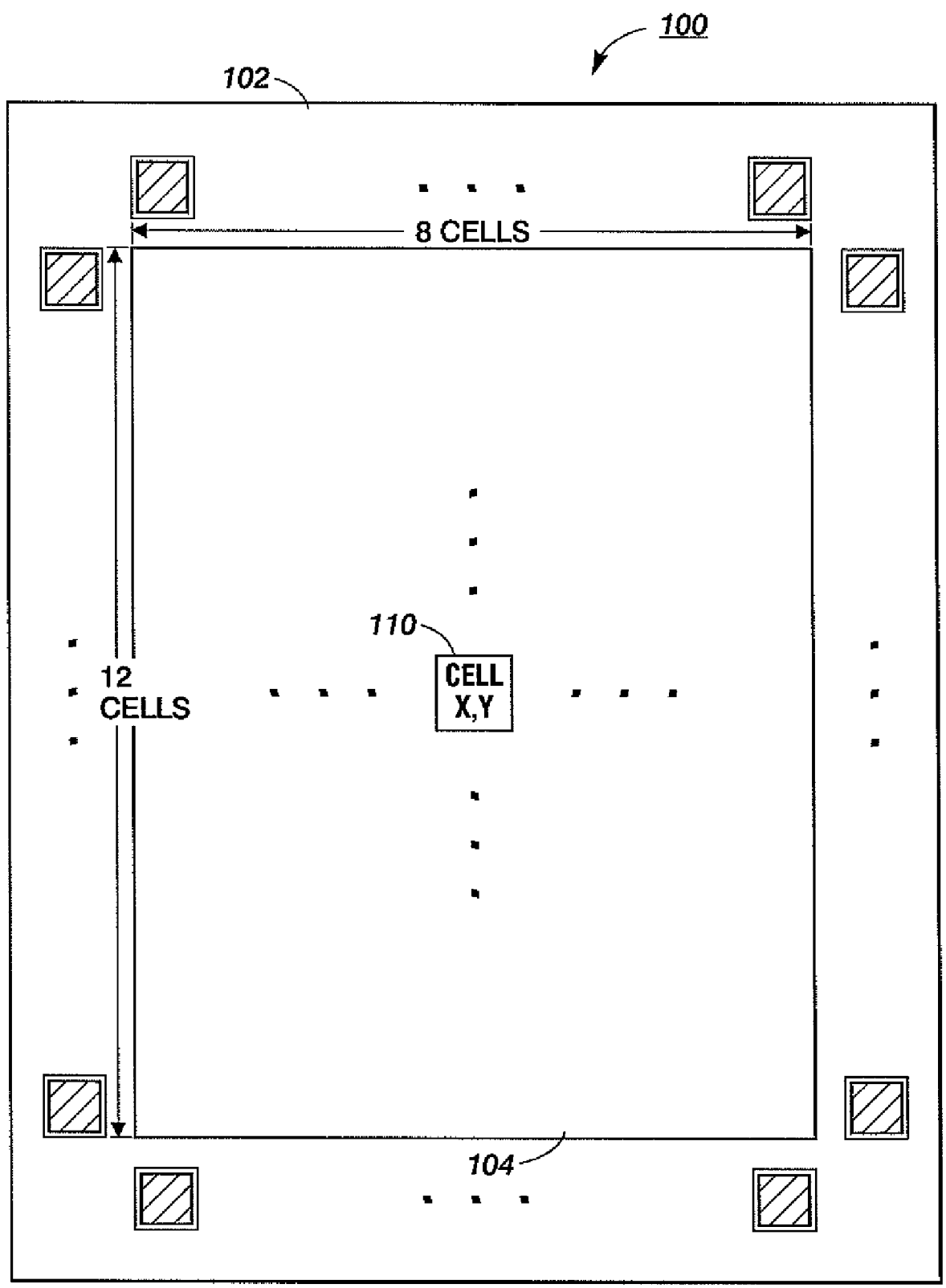
FIG. 2 is a schematic layout diagram of an integrated circuit (IC) that includes an array of thermal sensing cells on a flexible substrate and that can be used in calorimetry.

FIG. 2 shows integrated structure 100, which includes various components integrated on substrate 102, which can be a polymer layer or a silicon nitride layer, for example. As shown, the components of structure 100 include array 104, an 8×12 array of 96 thermal sensing cells. To interface with standard automated laboratory equipment, the cells are positioned on 9 mm centers and the automated laboratory equipment connects with contact pads of each cell. Array 104 can be one of several arrays fabricated on a single substrate.

Integrated structure 100 can, for example, be a calorimeter or nanocalorimeter array in which each cell can function as a calorimeter or nanocalorimeter. As used herein, a "nanocalorimeter" is a calorimeter capable of measuring in the range of nanocalories and use of a calorimeter to measure in the range of nanocalories is referred to herein as "nanocalorimetry;" measurement in the range of nanocalories is more generically referred to as "nanocaloric measurement."

Figure 3:
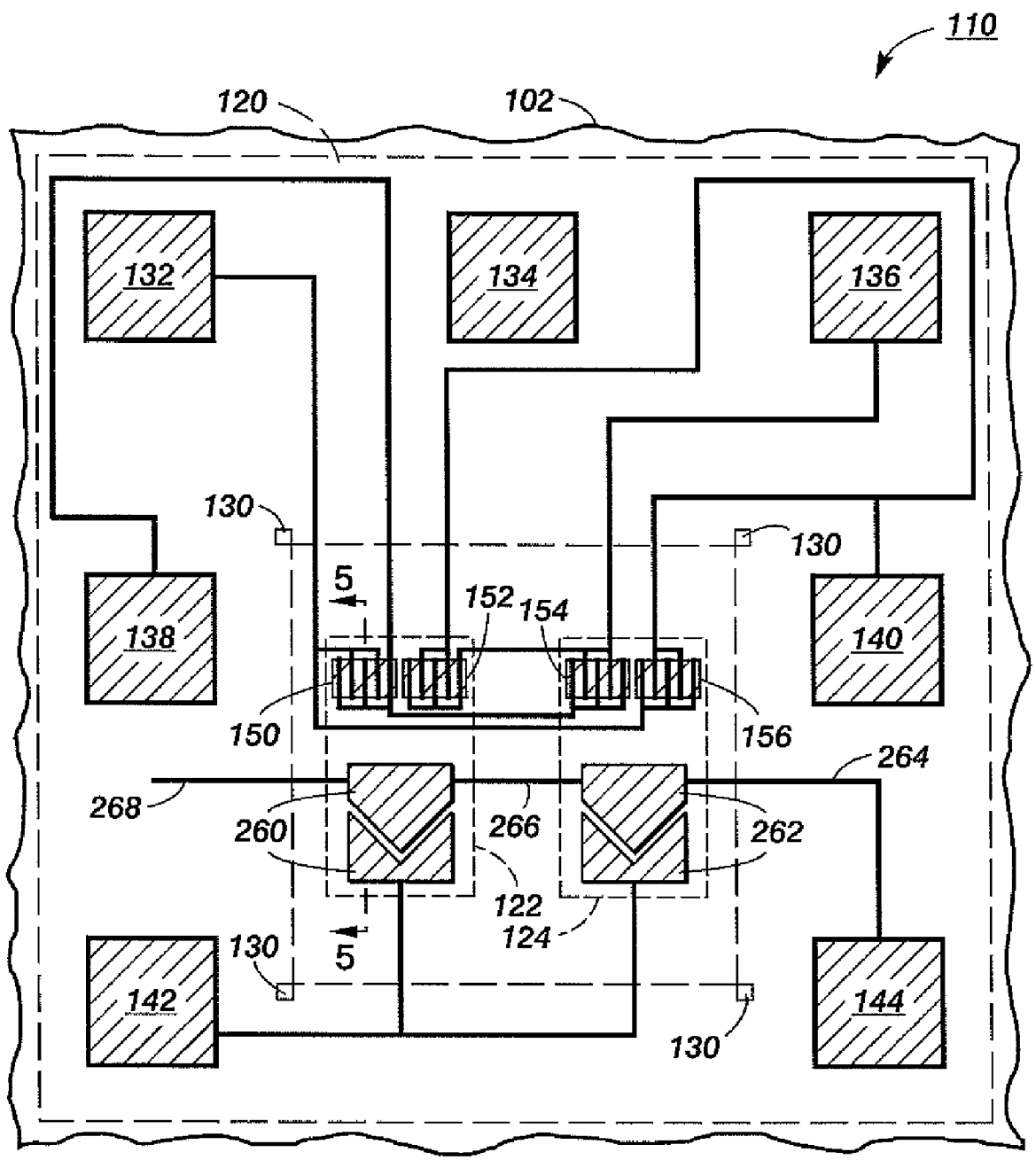
FIG. 3 is a partially schematic top view of a thermal sensing cell in the array of FIG. 2.

Within array 104, illustrative cell 110 could be implemented in any of a variety of ways, and all cells within array 104 could be substantially the same, although they could, in principle, be implemented differently. FIG. 3 shows an exemplary implementation of cell 110 in which it can operate to perform nanocalorimetry or nanocaloric measurement. Frame 120 (shown in dashed lines) supports substrate 102 from underneath. In addition, islands 122 and 124 (shown in dashed lines) are on the underside of substrate 102. Frame 120 illustratively has alignment structures 130 at the corners of a recess within which islands 122 and 124 are positioned. Frame 120 can, for example, be formed from 1 mm thick stainless steel in which alignment structures 130 and the recess for islands 122 and 124 are etched, and the recess can then provide thermal isolation between islands 122 and 124 as well as between either of the islands and frame 120. Thermal isolation could be maintained in various other ways.

Contact pads 132, 134, 136, 138, 140, 142, and 144 are on the upper surface of substrate 102 over frame 120. Each contact pad (except contact pad 134) is connected to one or more of the components over islands 122 and 124 by leads that are shown schematically in FIG. 3. If cell 110 is approximately square with 9 mm sides, the contact pads can be approximately 1 mm×1 mm, allowing connection with pogo pins. The leads can be approximately 50 μm wide or narrower; the leads could be even wider than 50 μm as long as they do not result in loss of thermal isolation.

Thermistor slabs 150, 152, 154, and 156 are arranged in two pairs, one including slabs 150 and 152 and the other including slabs 154 and 156. The contact pads could be connected in various ways to provide a bridge. For example, voltage $V_B$ can be applied to one of contact pads 132 and 136 while the other is connected to ground to provide a Wheatstone bridge with contact pad 138 connected to one intermediate node and with contact pad 40 connected to the other. Therefore, one of the thermistor slab pairs includes measuring thermistors while the other includes reference thermistors.

A "resistive thermal sensor" is a thermal sensor with electrical resistance that varies with the thermal stimulus that it senses, in contrast to various thermal sensors that sense in other ways such as with thermocouples or thermopiles. As used herein, the term "thermistor" means an electrically resistive component that includes semiconductor material with resistance that varies in response to a thermal change; a thermistor can therefore be employed in a resistive thermal sensor.

Figure 4:
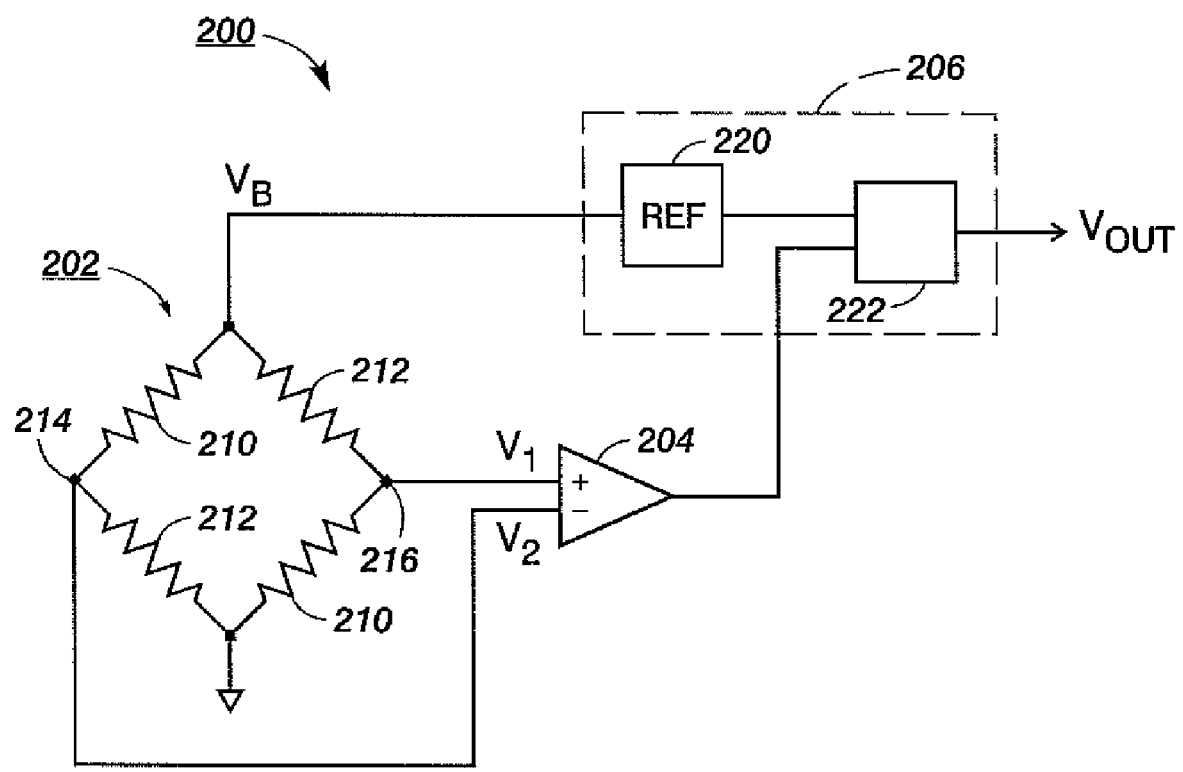
FIG. 4 is a schematic diagram of measuring circuitry that can be used with a cell as in FIG. 3.

Measuring circuitry 200 in FIG. 4 illustrates an example of a Wheatstone bridge as described above. Circuitry 200 includes thermistor bridge 202, difference amplifier 204, and lock-in amplifier 206.

The term "thermal input signal" refers herein to a signal provided to a component in the form of thermal change, and the thermistors in thermistor bridge 202 can receive different thermal input signals. Thermistor bridge 202 includes two pairs of opposite thermistors, arranged in a Wheatstone bridge that suppresses, to the first order, common-mode variations. Implementations of bridge circuitry and related techniques are described in greater detail in co-pending U.S. patent application Ser. No. 11/167,612, entitled "Thermal Sensing with Bridge Circuitry," published as U.S. Application Publication No. 2005/0254994 and incorporated herein by reference in its entirety.

Thermistors 210, referred to as "measuring thermistors," are located so that they are exposed to a thermal input signal that is being measured, while thermistors 212, referred to as "reference thermistors," are located to make a reference measurement. For example, if the thermal effect of a reaction is being measured, thermistors 210 can be located so that a thermal signal indicating heat from the reaction would be conducted or otherwise provided to them, while thermistors 212 can be located away from and insulated from the reaction so that they receive no such thermal signal.

Difference amplifier 204 amplifies the difference voltage between nodes 214 and 216 of bridge 202 and can be implemented as a low-noise, very high impedance amplifier; in current implementations, a printed circuit board (PCB) (not shown) that supports pogo pin connectors for a row of cells also has a row of eight difference amplifiers, one for each cell in the row, with each cell's difference amplifier 204 amplifying the difference voltage across its bridge 202 by approximately a factor of 100. The output from difference amplifier 204 is provided, through conditioning circuitry (not shown) and, optionally, multiplexing circuitry (not shown), to lock-in amplifier 206, which performs second stage amplification, removing additive voltage noise by bandwidth narrowing. The conditioning circuitry can, for example, include a conventional analog driver (not shown) to amplify current while maintaining the amplified voltage from difference amplifier 204 unchanged, providing an amplified analog signal that can drive lock-in amplifier 206 without signal degradation.

As noted above, multiplexing circuitry is optional, because each cell could have a respective lock-in amplifier 206, allowing concurrent analog-to-digital conversion for all cells in parallel; in a current implementation, however, multiplexing is performed, such as by measuring each cell in a row in series and then advancing to the next row, and the same multiplexing circuitry (not shown) also controls routing of merge signals to cells so that the cell receiving merge signals is also the cell being measured. Various other multiplexing techniques could be used with appropriate circuitry, such as for concurrent measuring of pairs, rows, or other appropriate groupings of cells in parallel.

The voltage VB provided to bridge 202 is a sinusoidal voltage, or "sine wave signal", derived from the internal reference voltage source 220 of lock-in amplifier 206; in a current implementation, the same PCB described above, with pogo pin connectors and difference amplifiers, also includes drive circuitry that amplifies the sine wave signal before providing it to each cell's bridge 202, and the circuitry on this board could also be treated as part of a calorimeter. Lock-in amplifier 206 also includes an amplifying component 222 that receives the reference voltage and the output from difference amplifier 204; component 222 performs operations such as filtering, bandwidth reduction, and amplification of the difference amplifier output and provides the output signal $V_{out}$. $V_{out}$ is proportional to the difference between the temperature sensed by the measuring thermistors 210 and the temperature sensed by the reference thermistors 212, and can be provided by lock-in amplifier 206 in both analog and digital forms.

To perform nanocalorimetry or nanocaloric measurement, circuitry 200 can generally be implemented with standard electrical components, except that bridge 202 includes thermistors that have particular noise properties under a device's operating conditions. For example, they can be low noise thermistors or they can be thermistors that include materials with specific noise characteristics. In a low noise implementation, difference amplifier 204 and other resistors (not shown) would also be selected for low noise characteristics under the device's operating conditions. The term "operating conditions" is used herein to refer to the relevant conditions under which a calorimeter or other thermal sensing device is designed to operate, such as dissipated power, bias voltage, ambient temperature, and so forth. Further information about low noise thermal sensors such as low noise thermistors is provided in co-pending U.S. patent application Ser. No. 11/167,748, entitled "Resistive Thermal Sensing," published as U.S. Patent Application Publication No. 2005/0238080 and incorporated herein by reference in its entirety.

In general, resolution of a temperature measurement made by circuitry 200 is limited by several factors, each of which can be characterized as an example of an intrinsic noise source as described above: thermistor noise; contact noise, such as from pogo pin contacts or other contacts; other electrical noise, such as from the amplifiers; temperature coefficient of resistivity (TCR) of each thermistor; maximum bridge supply voltage $V_B$ allowed; and limits in the common-mode rejection ratio of the Wheatstone bridge. By performing a noise analysis on an implementation of circuitry 200, it is possible to optimize electrical components for noise. For example, lock-in amplifier 206, with a reference frequency typically around 1000 Hz, suppresses most of the 1/f (low frequency) noise originating from the electronics itself or the environment. In current implementations, 1/f noise and most other intrinsic noise have been reduced to negligible levels under typical operating conditions, leaving thermistors and difference amplifiers as the dominant remaining intrinsic noise sources. Further information about noise optimization is included in co-pending U.S. patent application Ser. No. 11/167,612, entitled "Thermal Sensing with Bridge Circuitry," published as U.S. Application Publication No. 2005/0254994 and incorporated herein by reference in its entirety.

Although illustrated in FIG. 3 with thermistors as described above, cell 110 could be implemented with a variety of other resistive thermal sensors or thermal sensors of other types, such as thermocouples and thermopiles. Rather than semiconductor material, as in a thermistor, resistive thermal sensors could be made with other materials with a high TCR when compared with other materials. Examples of materials that have been used in resistive thermal sensors include, for example, platinum, nickel, copper, iron-nickel alloys such as balco, tungsten, iridium, oxides of nickel, manganese, iron, cobalt, copper, magnesium, and titanium, and other metals, metal alloys, and oxides of metal. Furthermore, it may be possible to produce resistive thermal sensors or other thermal sensors using other conductive or semiconductive materials.

FIG. 3 also shows drop mergers 260 and 262, on one of which a reaction can be caused so that differential temperature measurement can be performed. On the opposite side of substrate 102 from drop merger 260 and slabs 150 and 152 is a thermally conductive component, illustrated in FIG. 3 by island 122. When a reaction occurs within a fluid drop under control of drop merger 260, island 122 thermally couples the drop with slabs 150 and 152, providing a thermally conductive path from the drop to thermal sensors that include slabs 150 and 152. Similarly, island 124 thermally couples a fluid drop under control of drop merger 262 with slabs 154 and 156.

Conductive line 264 extends from pad 144 to the upper part of drop merger 262, conductive line 266 extends between the upper parts of drop mergers 260 and 262, and conductive line 268 extends leftward from the upper part of drop merger 260 to provide some symmetry with conductive line 264. Pad 142 is connected to the lower parts of both drop mergers by another conductive line.

Figure 5:
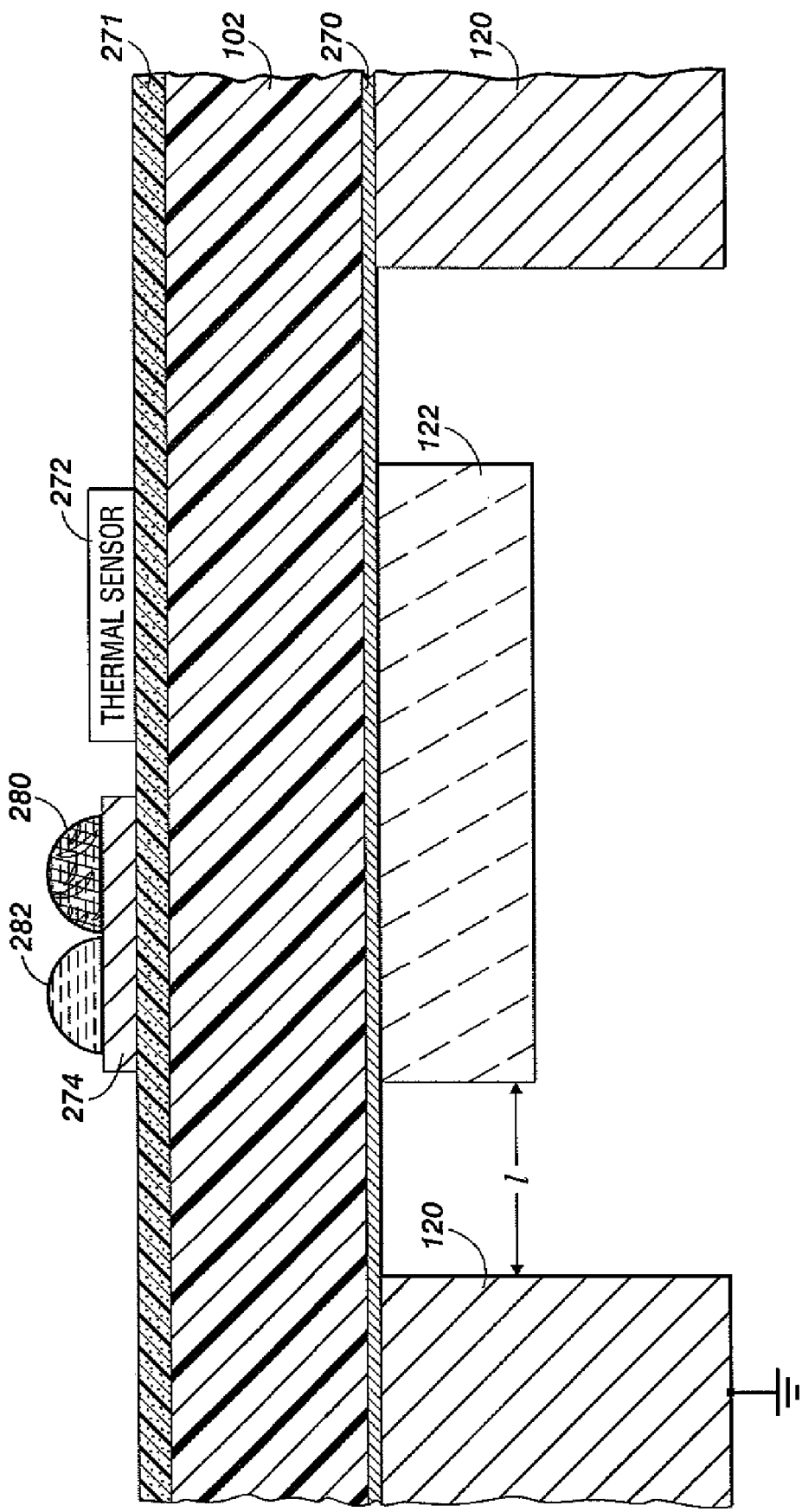
FIG. 5 is a partially schematic cross-sectional view of a cell as in FIG. 3, taken along the line 5-5.

The cross section in FIG. 5, taken along the line 5-5 in FIG. 3, illustrates additional features of an implementation of cell 110. As shown, frame 120 includes electrically conductive material and is connected to ground so that anti-coupling layer 270 can be grounded. Anti-coupling layer 270 could be over island 122 as shown in FIG. 5, or could be under island 122 or could be replaced by another anti-coupling component, as described in co-pending U.S. patent application Ser. No. 11/167,746, entitled "Thermal Sensing," published as U.S. Patent Application Publication No. 2005/0254552 and incorporated herein by reference in its entirety. Island 122 can include thermally conductive metal such as copper or aluminum at a thickness of 9 μm or thinner; in general, island 122 can include any thermally conductive material and desired conduction can be obtained by adjusting thickness in proportion to the material's thermal conductivity. Anti-coupling layer 270 could be implemented as a 10 nm thick layer of gold, to prevent capacitive coupling between adjacent parts of island 122. Because it is very thin, layer 270 has low thermal conductivity, preserving thermal isolation.

Frame 120 can also provide a thermally stable support for the multi-layered structure that includes substrate 102. Frame 120 can have a high thermal inertia.

In producing components on substrate 102, barrier layer 271 can be initially deposited on the upper side of substrate 102, protecting against contaminants and humidity and therefore increasing device performance. In a successful implementation, barrier layer 271 is a layer of approximately 300 nm of silicon oxynitride ($SiO_xN_y$). Then, various other components such as thermistors, conductive lines, electrodes, and additional layers to provide electrical passivation, environmental barriers, hydrophobic or oleophobic surfaces, or other properties can be produced. Additional techniques for producing components as shown in FIG. 5 are described in co-pending U.S. patent application Ser. No. 11/318,926, entitled "Producing Layered Structures Using Printing," and incorporated herein by reference in its entirety.

FIG. 5 also illustrates thermal sensor 272 and drop merger 274, each of which could be implemented as shown in FIG. 3 or in various other ways including those described in the co-pending applications incorporated by reference above. Drop merger 274 can be implemented, for example, with two or more electrodes that receive electrical signals to control drop merging, referred to herein as drop merger signals. For example, drop merger signals could include high voltage pulses received with opposite polarity on different electrodes, such as through conductive lines as described above in relation to FIG. 3. The circuitry connected to the conductive lines through the contact pads can include appropriate protection for amplifier circuitry, such as a switch or other component to decouple the amps during the high voltage pulse, or some other circuitry to protect against electrostatic damage.

In FIG. 5, target drop 280 containing target protein/nucleic acid or other target molecules and fragment drop 282 containing fragments have been deposited on the upper surface of drop merger 274. In addition to electrodes, drop merger 274 can include a covering layer of polymer or other appropriate material that can provide passivation, insulation, a hydrophobic or oleophobic upper surface, or other appropriate properties. Target drop 280, for example, can be deposited on the upper surface but positioned asymmetrically over a gap between electrodes with a proportion of drop 280 directly above a first electrode larger than the proportion above a second. Fragment drop 282, on the other hand, can be deposited entirely above the second electrode. Depositing drops or droplets as described above is but one example of an operation that "positions" samples, such as by positioning samples within a region; more generally, an operation "positions" a sample in a region if the operation begins with the sample not in the region and ends with the sample in the region.

After drops 280 and 282 have been deposited and have reached thermal equilibrium, a signal source (not shown) can provide a high voltage pulse across the two electrodes, causing drop 280 to be propelled leftward toward stationary fragment drop 282, and therefore causing the two drops to merge; various other signals could be provided to various combinations of electrodes to cause drops to merge, including those described in U.S. Patent Application Pub. No. 2006/0132542, incorporated herein by reference in its entirety. The merged drops can mix by diffusion, and the high voltage pulse can also be sufficiently strong that the two drops mix more quickly after they have merged; their mixing initiates a reaction between target molecules in drop 280 and fragments in drop 282.

A reaction between target molecules and fragments produces a thermal input signal that includes not only a component indicating enthalpy from the reaction, but also an extrinsic noise component resulting from various sources, such as evaporation, convection, and conduction, described in greater detail in U.S. Patent Application Publication No. 2005/0254994, incorporated herein by reference in its entirety.

The thermal input signal is then conducted downward through the layered structure that includes drop merger 274, barrier layer 271, substrate 102, and anti-coupling layer 270, reaching island 122. Island 122 conducts the thermal signal laterally to a region under thermal sensor 272 where the signal is conducted upward through the layered structure to thermal sensor 272. At the same time, a reference reaction can occur on drop merger 262, providing a reference thermal signal that similarly reaches the respective thermal sensor through island 124. A change in temperature in the measurement thermistors changes their resistance, resulting in detection of a current through bridge 202 (FIG. 4), which would be balanced if resistance were the same as that of the reference thermistors. The current's magnitude indicates the temperature difference between the measuring thermistors and the reference thermistors.

Figure 6:
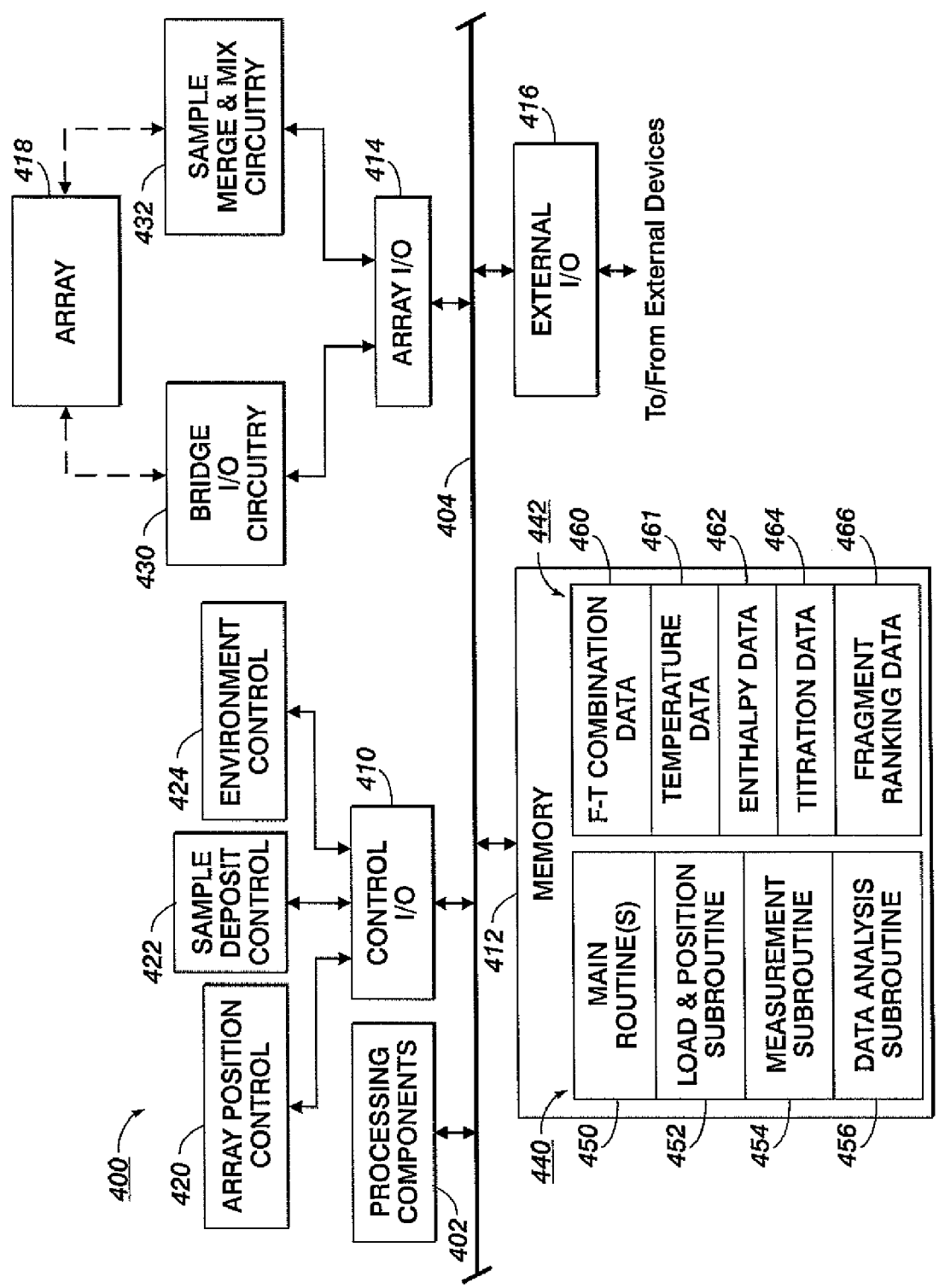
FIG. 6 is a schematic diagram of a system that can operate measuring circuitry as in FIG. 4 with cells as in FIG. 5 to rank fragment types that react with target types.

FIG. 6 shows system 400, an example of a system in which techniques as described above can be implemented, such as to rank fragment types that react with target types. As described below, system 400 can be implemented with a number of processing components and with operations that are partially automated, but it is foreseeable that system 400 can be implemented with a single processing component in a fully automated implementation, which could be advantageous.

System 400 illustratively includes processing components 402, which can include one or more central processing units (CPUs), each having a respective monitor and keyboard or other appropriate user interface as well as appropriate memory and peripherals and being connected to various other components through bus 404 or another suitable network or other interconnection structure, but a wide variety of other architectures could be employed, including any appropriate combination of hardware and software, as well as specialized hardware components such as application specific integrated circuits (ASICs) for one or more of the illustrated components or in place of a software component executed by a CPU in processing components 402.

System 400 also includes control input/output (I/O) component 410, memory 412, array I/O 414, and external I/O 416, all connected to bus 404. System 400 can include various other components (not shown) connected to bus 404. In addition to connections through external I/O 416 by which signals can be provided to and received from external devices, bus 404 can also be connected directly to components outside of system 400.

Control I/O 410 permits CPUs in processing components 402 to communicate with and control certain components of system 400 other than circuitry that provides signals to and receives signals from array 418, which could be implemented as an array on an integrated structure (FIG. 2).

In general, at least one CPU in processing components 402 performs automatic or partially automatic control through control I/O 410 and the same CPU or another also obtains analog output signals from array 418 automatically or partially automatically through array I/O 414. For interactive applications, however, control I/O 410 could itself also be connected to a suitable user interface, such as a monitor and keyboard (not shown). In the exemplary implementation in FIG. 6, array position control 420, also referred to as a "robot", can include devices for holding, covering, and moving a structure that supports array 418 and circuitry for controlling such devices. Sample deposit control 422 can similarly include one or more sample reservoirs, fluidic devices for providing samples of material from the reservoirs, and circuitry for controlling the devices. Environment control 424 can include a variety of structures and devices to control the atmosphere around array 418, including the composition of gases and the level and type of humidity, and the temperature around and within array 418; for example, environment control 424 could include devices to change the combination of gases in a chamber containing array 418, to control the level of humidity in the atmosphere through evaporation or condensation of a solvent also used in the samples, and to capture and dissipate heat generated by circuitry and other components of system 400 so that it cannot reach array 418.

In the illustrated implementation of system 400, array I/O 414 is a similar I/O component that permits at least one CPU in processing components 402 to communicate with several circuitry components that can, in turn, be electrically connected to circuitry in array 418. In the illustrated implementation, array I/O 414 is connected to bridge I/O circuitry 430 and sample merge and mix circuitry 432. Sample merge and mix circuitry 432 can include circuitry that provides appropriate voltage signals to electrodes in drop mergers 260 and 262 (FIG. 3), such as through the same multiplexing circuitry to pads 142 and 144 of a cell being measured.

Bridge I/O circuitry 430 can be implemented by circuitry that receives and compares voltage across nodes of each cell's bridge, such as with difference amplifier 204 and lock-in amplifier 206 (FIG. 4). Bridge I/O circuitry 430 also includes circuitry to convert analog output signals to digital form so that array I/O 414 can provide digital signals to a CPU in processing components 402 through bus 404; for this purpose, bridge I/O circuitry 430 can include lock-in amplifier 206 or any other suitable analog-to-digital conversion circuitry (not shown), together with related circuitry such as preconditioning components and so forth. Bridge I/O circuitry 430 can also include driving and multiplexing circuitry that amplifies a sine wave from internal reference voltage source 220 of lock-in amplifier 206 (FIG. 4) and provides the amplified sine wave signal to a node of each cell's bridge, such as through one of contact pads 132 and 136 (FIG. 3).

Sample merge and mix circuitry 432 can include circuitry that provides appropriate voltage signals to electrodes in drop mergers 260 and 262 (FIG. 3). For example, sample merge and mix circuitry could employ the same multiplexing circuitry as bridge I/O circuitry 430, providing signals to pads 142 and 144 of a cell being measured.

In general, circuitry 430 and 432 could be implemented in parallel for each of a number of cells, such as all the cells of a row of array 418, or could be implemented together with multiplexing circuitry (not shown) that would connect to each cell in sequence, as described above.

Memory 412 illustratively includes program memory 440 and data memory 442, although instructions for execution by each CPU in processing components 402 and data accessed during execution of instructions could be provided in any suitable way, including through external devices or components. The routines stored in program memory 440 illustratively include main routine(s) 450, load and position subroutine 452, measurement subroutine 454, and data analysis subroutine 456; rather than separate subroutines, all of the instructions in program memory 440 could be combined into a single routine, and program memory 440 could store various alternative or additional routines and subroutines (not shown) that a CPU in processing components 402 could call in executing any of main routine(s) 450. Similarly, the data in data memory 442 illustratively include fragment-target (F-T) combination data 460, temperature data 461, enthalpy data 462, titration data 464, and fragment ranking data 466, but could include various alternative or additional items of data and data structures accessed by a CPU in processing components 402.

In executing one of main routine(s) 450, a CPU in processing components 402 can, for example, continuously or periodically monitor and control environmental conditions, receiving information about environmental conditions from environment control 424 and providing signals to environment control 424 to modify conditions as necessary. In addition, the same CPU or one or more other CPUs in processing components 402 can call subroutines 452, 454, and 456 in sequence to automatically or partially automatically obtain fragment ranking data 466 for a set of fragment types that react with target types, during or after which any of main routine(s) 450 can again call load and position subroutine 452 to move the structure supporting array 418 out of position so that another such sequence can be performed.

In executing subroutine 452, a CPU can provide signals to array position control 420 to position the structure supporting array 418 for deposition of samples, such as in a loading chamber. Then, the CPU can provide signals to sample deposit control 422 to deposit desired samples on array 418 in accordance with F-T combination data 460; F-T combination data 460 can indicate, for each cell of array 418, the fragment type(s) and target type(s) to be included in its fragment and target samples respectively, and, when appropriate, concentrations of fragment and target types, and the CPU can use this information to control deposition of an appropriate set of four samples on each cell of array 418. At this time, a photographic or other appropriate image can be taken to allow visual or automatic determination whether the samples are in appropriate positions and whether they have pre-merged, after which appropriate adjustments can be made if necessary; for example, the same material could be redeposited on an available cell to avoid the need to clean the deposition tips for a new aspiration and also to avoid wasting a larger volume of scarce and expensive materials by having to refill the titer plate reservoir, which could consume about 100 μL of material in order to obtain a few drops, each 250 nL or less. In appropriate cases, a decision might similarly be taken to redo an entire experiment to obtain more information about the same materials before refilling the titer plate reservoir with a different material.

When satisfactory combinations of samples have been deposited in the cells, the CPU can again provide signals to array position control 420 to prepare it for a measurement operation, such as by covering array 418 with a cap and providing an appropriate combination of gases under the cap, with the structure that supports array 418 also being moved into a position at which it is connected with circuitry 430 and 432, such as by raising array 418 so that contact pads in one or more cells engage pogo pins (not shown) on a PCB as described above. During these operations, photographic or other appropriate images of array 418 can be monitored for any apparent malfunction, in which case appropriate corrective measures can be taken, depending on the nature of the malfunction. Examples of how these operations can be performed are described in U.S. Patent Application Publication No. 2005/0254994, incorporated herein by reference in its entirety.

In executing subroutine 454, a CPU can provide signals to bridge I/O circuitry 430, causing it to drive a set of bridges in array 418, causing the bridges to self-heat to a temperature that equilibrates sample temperature with the controlled environment around array 418. After the samples reach thermal equilibrium, the CPU could provide signals to array position control 420 to cause array 418 to be positioned in a measurement chamber while maintaining contact with the pogo pins. Prior to measurement, array 418 can be held stable for an appropriate period, such as 2-4 minutes, to ensure thermal equilibrium. Then the measurement sequence can be initiated by again providing signals to bridge I/O circuitry 430 so that it drives the bridges.

During measurement, each bridge can be zeroed by properly setting an offset voltage within difference amplifier 204 (FIG. 4). Thermal equilibration can then be confirmed by operating bridge I/O circuitry 430 to measure voltage across the bridge for a short period of time; when the rate of change is below a pre-specified threshold level, as visually observed on a display or as automatically determined by the CPU, thermal equilibrium has been reached. The zeroing operation may be repeated as necessary by the CPU in executing measurement subroutine 454.

After zeroing, the CPU automatically or in response to operator action can start a measurement period during which digital heat values are obtained continuously from one or more lock-in amplifiers in bridge I/O circuitry 430 for an appropriate period of time such as 4-10 minutes. More specifically, during this period, the imbalance voltage of each bridge in a row or other set of cells can be repeatedly measured to obtain a series of output analog signals, which can then be converted to digital temperature values, i.e. values indicating temperature differences, by one or more lock-in amplifiers or other appropriate components in bridge I/O circuitry 430.

After an initial sampling period such as 30 seconds, the CPU can also provide signals to sample merge and mix circuitry 432, causing the samples in a row or other set of cells to merge and mix in parallel; this can be accomplished by applying a drop moving voltage through one of pads 142 and 144 (FIG. 3) in each cell in the set. Rather than obtaining digital temperature values continuously, transient voltages generated from the merging voltages could be allowed to dissipate, such as by temporarily pausing operation. In any case, digital temperature values obtained during the remainder of the measurement period, e.g. during an additional appropriate period such as 2-8 minutes depending on the reaction being measured, indicate enthalpy released during the resulting reaction based on the voltage imbalance in each cell's bridge and a time series of digital temperature values for each measured reaction can then be stored in temperature data 461 in memory 412 for later automatic or manual analysis or can be immediately provided to one of the CPUs in processing components 402 for automatic real-time analysis. Before storing digital temperature values, the CPU could perform a scaling operation on each value, such as multiplying it by a constant that converts it to a temperature value scaled in a desired way, thus producing a time series of scaled digital temperature values; the constant could be based, for example, on a combination of TCR, amplifier gain, and other factors. Several ways of implementing measurement subroutine 454 are described in U.S. Patent Application Publication No. 2005/0254994, incorporated by reference above.

During and after completion of measurement, various other operations can be performed, such as by executing load and position subroutine 452, to move the array back to the loading chamber. Photographic or other appropriate images can be obtained and analyzed manually or automatically to verify that both pairs of samples in each cell merged and that other identifiable malfunctions did not occur.

Figure 7:
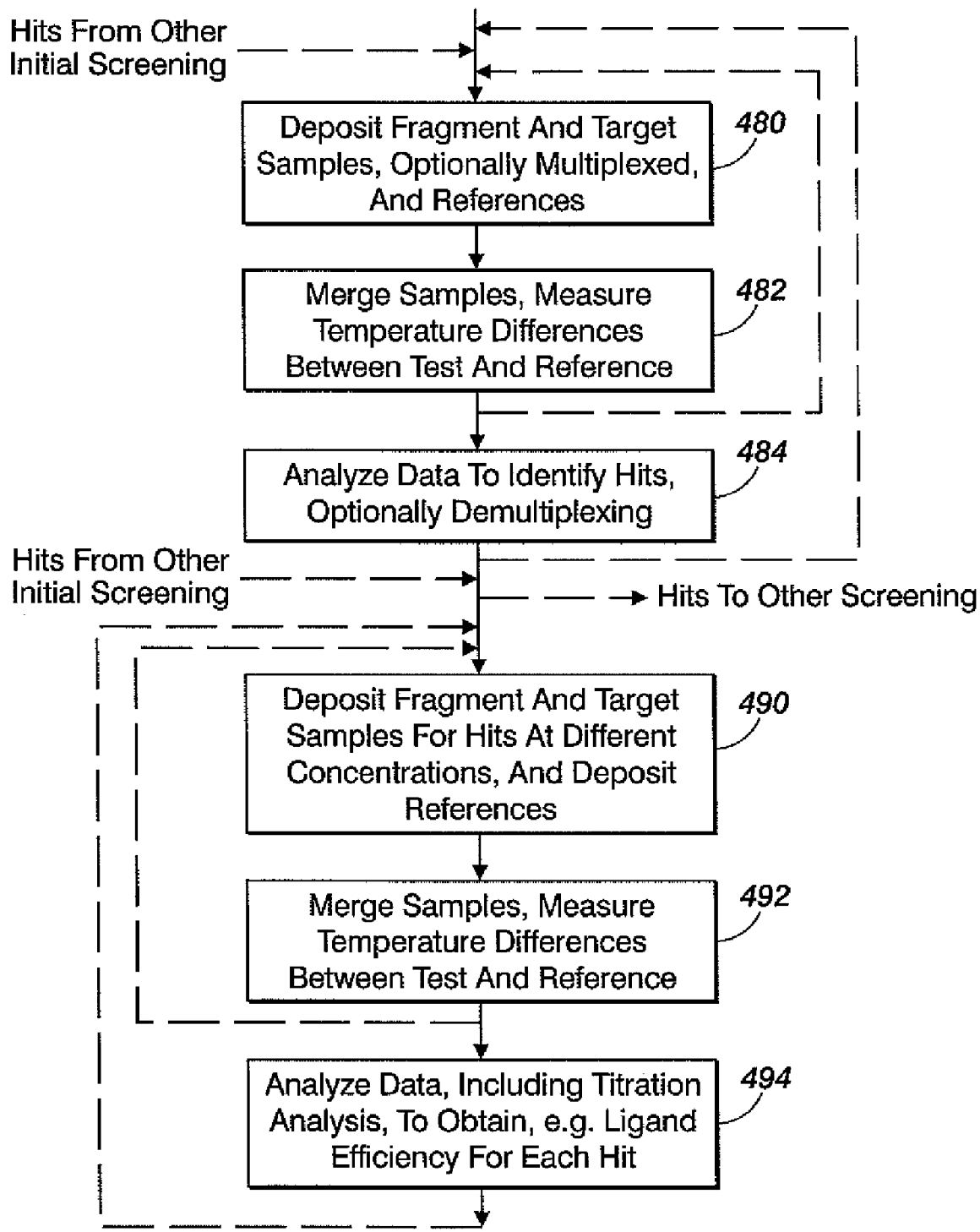
FIG. 7 is a flow chart showing operations of a system as in FIG. 6 in ranking fragment types that react with target types.

FIG. 7 illustrates general operations in FBS techniques that could be performed with system 400 in FIG. 6 to implement a two-stage screening strategy. The operations in boxes 480, 482, and 484 can be characterized as "initial screening", while the operations in boxes 490, 492, and 494 can be characterized as "titration-based screening".

The operation in box 480 begins initial screening by depositing fragment samples and target samples for one or more fragment-target combinations on array 418, together with respective reference samples. Fragment-target combinations could be chosen for initial screening in any appropriate way, including well-known approaches that use libraries of compounds or other initial screening techniques as indicated by a dashed arrow into box 480. The operation in box 480 can optionally deposit multiplexed fragment or target samples, similarly to techniques in which drops containing plural drug targets and drops containing plural drug candidates are deposited as described in U.S. Patent Application Ser. No. 2003/0186455, incorporated herein by reference. In either case, the operation can be implemented by executing load and position subroutine 452 as described above. For an initial screen, an appropriate concentration is likely to be a few millimolar, providing a rough screen in the sense that fragment types with $K_d$ much greater than a few millimolar will not give a large signal. Although each fragment-target combination can be deposited in more than one cell, the operation in box 480 would not ordinarily be implemented with different concentrations during initial screening, because one purpose of initial screening is to identify reacting fragment-target combinations without performing complex titration analysis.

With the samples deposited, the operation in box 482 merges samples within cells of array 418 while measuring temperature differences between test and reference thermal signals, obtaining for each cell a respective time series of digital temperature values that is stored in temperature data 461. The operation in box 482 can be implemented by executing measurement routine 454 as described above. As suggested by the dashed line from box 482 back to box 480, several iterations of the operations in boxes 480 and 482 can be performed before continuing with subsequent operations, resulting in a larger body of data to be analyzed.

The operation in box 484 then analyzes the data from box 482 to identify hits, i.e. fragment types that reacted with a target type according to an appropriate criterion. The operation in box 484 can be implemented by executing data analysis subroutine 456, such as with operations described below for exemplary implementations. As suggested by the dashed line from box 484 back to box 480, a session of initial screening can include several iterations of the operations in boxes 480, 482, and 484, continuing for example until a desired number of fragment-target combinations have been tested or until a desired number of hits have been identified. Also, if multiplexed samples were deposited in box 480, the operation in box 484 can initiate one or more additional iterations of boxes 480, 482, and 484 to "demultiplex", such as by separately providing each multiplexed fragment type from a hit with the same target type.

The operation in box 484 is an example of ranking fragment types because it provides, for a given target type, a set of one or more fragment types that react with it. The identified fragment types in the set are distinguished from other fragment types that do not react with the target type and therefore are not included in the set.

Box 490 then begins titration-based screening on a set of hits, such as combinations identified in box 484; as indicated by a dashed line entering box 490, however, part or all of the set of hits could be identified by another initial screening operation rather than from box 484, such as by X-ray crystallography or NMR techniques; similarly, as indicated by a dashed line exiting box 484, hits identified in box 484 could be used in another, more detailed screening operation, such as by X-ray crystallography or NMR techniques, rather than titration-based screening as in boxes 490, 492, and 494.

The operation in box 490 begins titration-based screening by depositing fragment samples and target samples on array 418 for one or more of the set of hits, together with respective reference samples. In contrast with box 480, the operation in box 490 deposits samples that include different concentrations for each fragment type, allowing for subsequent titration analysis; on the other hand, the operation in box 490 would not ordinarily be implemented with multiplexing of fragment or target types in a sample. Concentrations for fragment types and target types could be chosen for titration-based screening in any appropriate way, including well-known titration techniques. As in box 480, the operation in box 490 can be implemented by executing load and position subroutine 452 as described above.

With the samples deposited, the operation in box 492 merges samples within cells of array 418 while measuring temperature differences between test and reference thermal signals, obtaining for each cell a respective time series of digital temperature values that is stored in temperature data 461. As in box 482, the operation can be implemented by executing measurement routine 454 as described above. As suggested by the dashed line from box 492 back to box 490, several iterations of the operations in boxes 490 and 492 can be performed before continuing to subsequent operations, resulting in a larger body of data to be analyzed; it would also be possible to implement each iteration of boxes 490 and 492 with respective uniform concentrations, but with differences between concentrations deposited in different iterations.

The operation in box 494 then analyzes the data from box 492 to rank fragment types, such as in ways mentioned above in relation to FIG. 1. More specifically, the analysis in box 494 includes titration analysis, which can be implemented by executing data analysis subroutine 456, such as with operations described below for exemplary implementations. As suggested by the dashed line from box 494 back to box 490, a session of titration-based screening can include several iterations of the operations in boxes 490, 492, and 494, continuing for example until a desired number of hits have been further ranked or until a fragment type has been discovered whose reaction with a target type meets an appropriate criterion.

The operation in box 494 is therefore another example of ranking fragment types because it provides, for a given target type, distinguishing information about how each of a set of fragment types reacts with it. The information can be a value for each fragment type, such as $K_d$ or a ligand efficiency, or it can be a rank ordering of fragment types, such as in accordance with ligand efficiency or binding strength.

Figure 8:
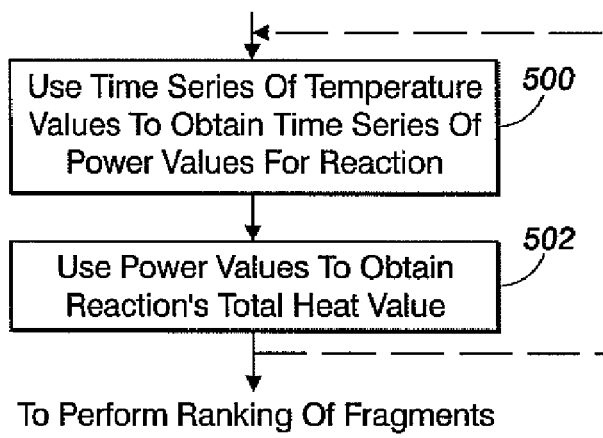
FIG. 8 is a flow chart showing operations in an implementation of data analysis as in FIG. 7.

FIG. 8 illustrates an example of operations that could be performed by a CPU in executing data analysis subroutine 456 in either of boxes 484 or 494 using temperature data 461 from one of boxes 482 or 492, respectively. The operations in FIG. 8 could be fully automated, but need not be—the implementation described below involves some human participation in analysis.

Box 500 shows an initial operation in which a reaction's time series of scaled digital temperature values from temperature data 461 is accessed and used to obtain a corresponding time series of power values for the reaction. As used herein, the term "power value" refers to a value that indicates rate of heat release or absorption during a reaction. The operation in box 500 could also adjust values in various ways: One prototype implementation, for example, allows for scaling similar to the scaling operations described above, which could be useful if a different TCR value is discovered after measurement; the prototype implementation also performs baseline adjustments in the process of obtaining power values.

Baseline adjustments could be implemented in many different ways, and are important because baseline drift can occur in complex ways during a measurement operation; for example, rather than simple baseline drift throughout a measurement session, a thermal shift could occur after droplets are merged. In this context, a "thermal shift" is a change in baseline from one temperature to another due to a change in the differential thermal dissipation between test and reference samples, and such a change occurs with a characteristic time of the thermal dissipation during measurement; for example, if merged test drops attain a different shape than merged reference drops, the difference in shape can result in a different baseline, since thermal dissipation depends in part on the drops' surface areas.

Then, baseline correction is made by curve fitting values that occur in the temperature time series before merge to obtain a pre-merge baseline and by also curve fitting values that occur after baseline return to obtain a post-return baseline; in a current implementation, both pre-merge and post-return baselines have been successfully obtained by doing respective linear fits. The post-return baseline fit can then be adjusted by subtracting a constant equal to its value at merge time, so that the pre-merge baseline fit and the adjusted post-return baseline fit are equal at merge time. As a result, the pre-merge and post-return baseline fits can be combined into a single baseline time series that includes a baseline value for each value in the temperature time series. Each value from the baseline time series can then be subtracted from the counterpart value in the temperature time series, producing a time series of baseline corrected temperature values.

The baseline corrected temperature values can then be used in a preliminary baseline adjustment in which baseline shift can occur. In a prototype implementation, temperature values are multiplied by precomputed matrices based on a thermal model for the response of the calorimeter to a pulse of heat generated in a drop; then, linear solutions are performed to obtain power values as a function of time in sufficiently small chunks to allow fast calculation. A commercial modeling software package such as from COMSOL, Inc. can be used to model the calorimeter's thermal response to a pulse of heat generated in the drop, taking into account its noise sources, and the result can then be used to obtain the precomputed matrices, which can be chosen in accordance with the data set size on which baseline adjustment is performed. The operation in box 500 can therefore perform deconvolution as described above, because it can extract a signal component from the baseline corrected temperature values. For speed of calculation, a program can be written in the Matlab® language from The MathWorks, Inc. to perform matrix multiplication and linear solutions.

In another approach, one could perform measurements on sites in an array with integrated heaters. For example, a known amount of power could be introduced by a resistive heater by applying a voltage to the heater beginning at a defined point in time, and the temperature rise could be monitored as it changes to a new steady state. The derivative of this temperature response could then be used as a model for the impulse response, which is then used to obtain the precomputed matrices.

As part of the operation in box 500, a time series of temperature values can be computed from the time series of power values, using the pulse response mentioned above. The two time series can be plotted and displayed to an operator, allowing the operator to check their fit and, if necessary, make adjustments.

A reaction's time series of power values from box 500 can then be used in box 502 to obtain a total heat of the reaction. In a straightforward implementation, for example, the operation in box 502 can integrate power over the time of the reaction; a simple way to implement this would be to take a summation of the power values from box 500 over the entire series or between beginning and ending times of the reaction identified in any appropriate way.

The operations in boxes 500 and 502 can be performed for a number of reactions, as suggested by the dashed line running from box 502 back to box 500. In other words, the operations in boxes 500 and 502 can be performed for one reaction at a time, then for the next reaction, etc.; or the operations could be performed for each reaction in any other appropriate way. The end result is a total heat value for each reaction, and the total heat values can be stored in enthalpy data 462.

Figure 9:
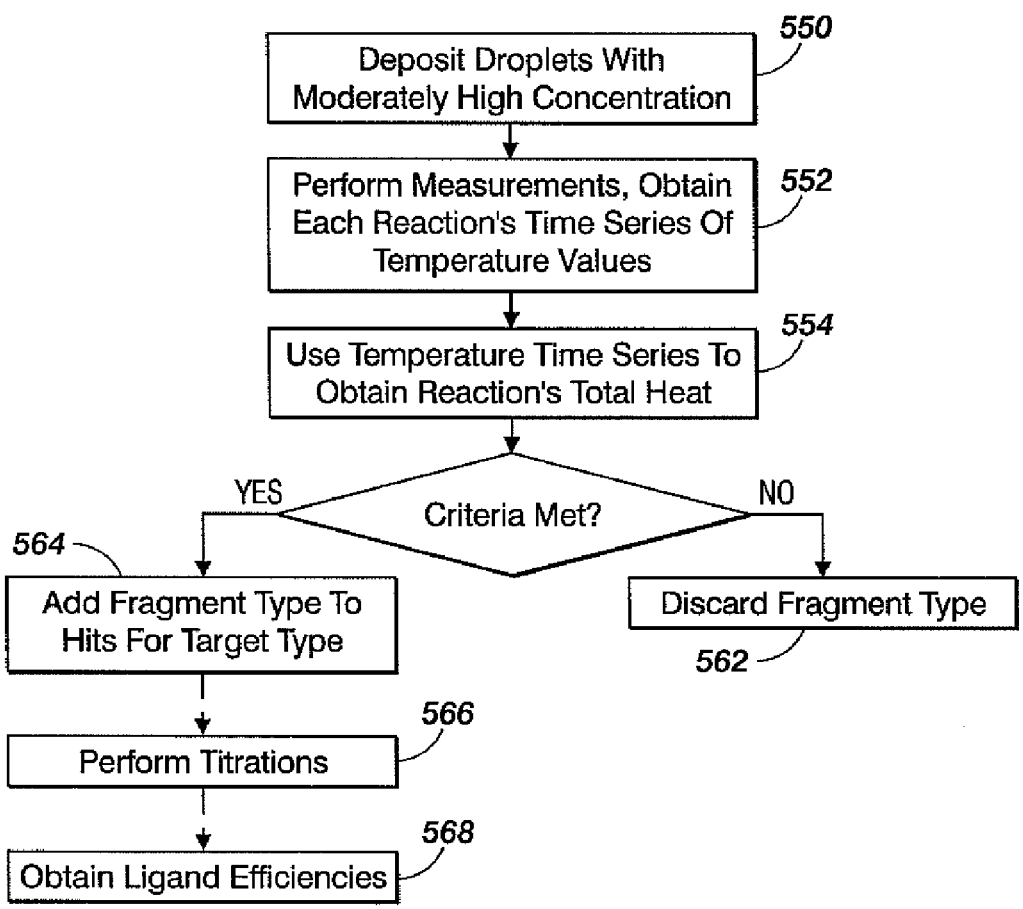
FIG. 9 is a flow chart showing operations in an implementation of initial screening of fragment types as in FIG. 7.

FIG. 9 illustrates one way to implement initial screening in boxes 480, 482, and 484 (FIG. 7), employing data analysis similar to that described in relation to FIG. 8. As in FIG. 8, the operations in FIG. 9 could be fully automated, but the described implementation involves some human participation.

The operation in box 550 implements the operation in box 480 by depositing test and reference sample pairs in a number of cells of array 418. The test samples in all the cells can, for example, all have the same concentration of fragment types, at a moderately high concentration that is not so high that it always results in a reaction but is high enough that it seldom causes a false negative; for many fragment types, a concentration of a few millimolar will meet this criterion. Similarly, the test target samples in all the cells can all have equal, moderately high concentrations of a target molecule type, with lower concentration being better up to the limit of device sensitivity.

The operation in box 552 implements the operation in box 482 by performing a measurement operation in the manner described above for each of the cells, saving a time series of temperature values for each cell's reaction. As mentioned above, each reaction's temperature time series can be stored in temperature data 461 (FIG. 6).

The operation in box 484 (FIG. 7) is implemented by boxes 554, 560, 562, and 564 in FIG. 9. The operation in box 554 uses the time series of temperature values to obtain each reaction's total heat, which can be implemented as described above in relation to boxes 500 and 502 (FIG. 8). The operation in box 560 applies an appropriate criterion to the total heat values from box 554 to determine whether the fragment-target combination's heat of reaction between the target type and each fragment type is sufficient to justify titration-based screening or other further screening, i.e. whether a reaction occurred when they were merged. If not, the fragment type is discarded, in box 562. But if box 560 determines that a reaction did occur, the operation in box 564 then adds the fragment type to the hits that have been found, such as by storing identifying information for the fragment type in memory. The technique in FIG. 9 could then be again performed for further fragment types to find more hits; when an appropriate set of hits have been found, titration-based screening can be performed on the hits, such as by performing titrations in box 566 and obtaining ligand efficiencies in box 568.

The operation in box 560 could be implemented in various ways. For example, if a given number of reactions were measured for a given fragment type in box 552, a criterion can be applied separately to the total heat from each reaction and a decision on the fragment type can then be based on whether more than half the reactions meet the criterion; alternatively, a criterion could be applied to an averaged or otherwise combined heat for all the reactions. A criterion can be chosen to distinguish fragment types that are better than a control that has been fully evaluated, such as by merging the same target type with a buffer sample; the criterion can determine whether a reaction's total heat is significantly different than that of the control combination.

Figure 10:
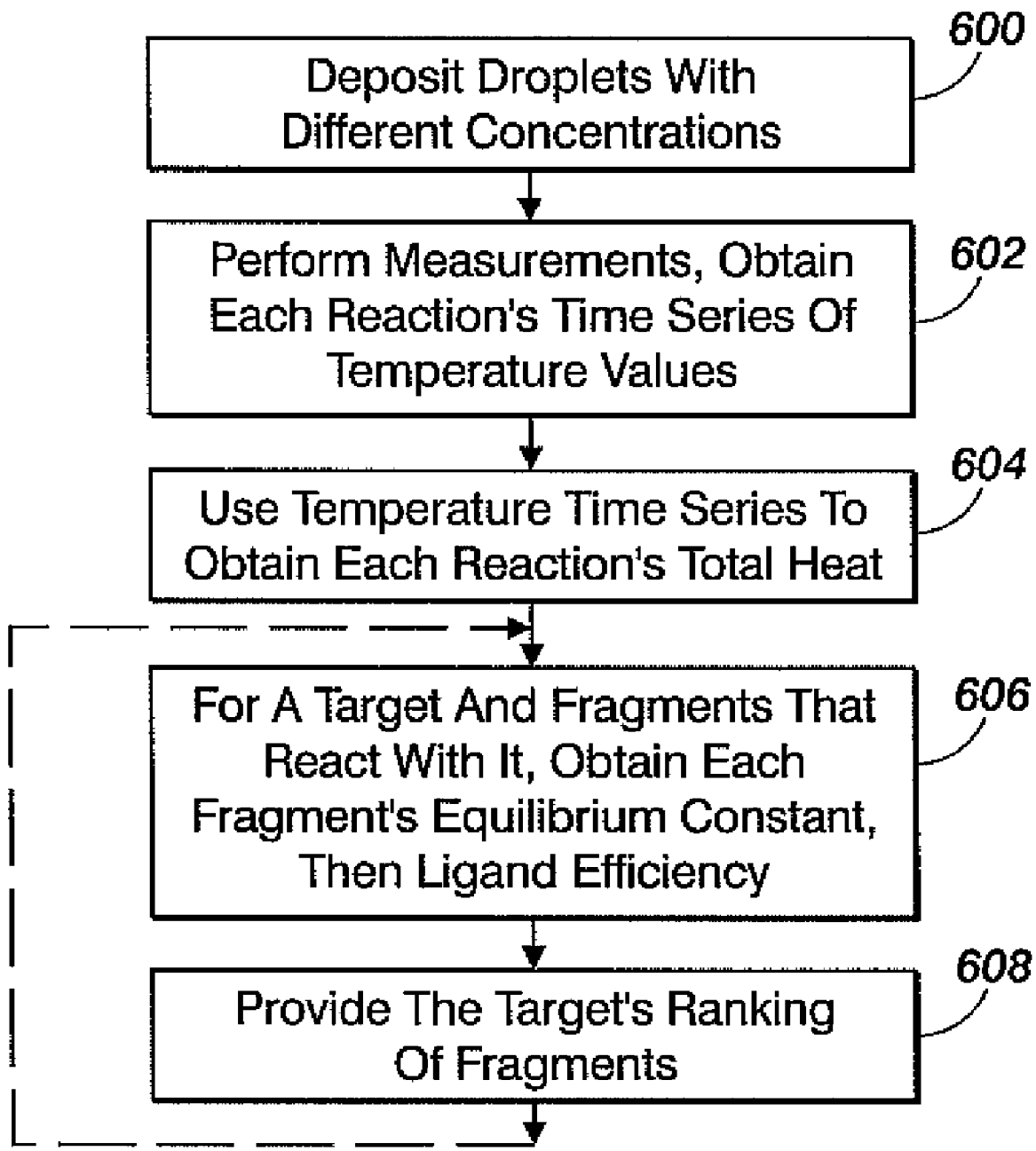
FIG. 10 is a flow chart showing operations in an implementation of titration-based screening of fragment types as in FIG. 7.

FIG. 10 illustrates one way to implement titration-based screening in boxes 490, 492, and 494 (FIG. 7), also employing data analysis similar to that described in relation to FIG. 8. As with FIGS. 8 and 9, the operations in FIG. 10 could be fully automated, but, as described, involve some human participation in analysis.

The operation in box 600 implements the operation in box 490 by depositing test and reference sample pairs in a number of cells of array 418. Test target samples with a given target type are deposited with test fragment samples that each have one fragment type; the test fragment samples deposited with a given target type, however, have different concentrations, chosen by appropriate techniques to obtain data suitable for titration calculation.

The operation in box 602 implements the operation in box 492 by performing a measurement operation in the manner described above for each of the cells, saving a time series of temperature values for each cell's reaction. As mentioned above, each reaction's temperature time series can be stored in temperature data 461 (FIG. 6).

The operation in box 494 (FIG. 7) is implemented by boxes 604, 606, and 608 in FIG. 10. The operation in box 604 uses the time series of temperature values to obtain each reaction's total heat, which can be implemented as described above in relation to boxes 500 and 502 (FIG. 8).

For a given target type and fragment types that react with it, the operation in box 606 uses the total heats from box 604 to obtain an equilibrium constant such as $K_d$ for each fragment type, and also uses each fragment type's $K_d$ to obtain its ligand efficiency. For example, F-T combination data 460 could be accessed to retrieve the fragment types and concentrations for cells in which the target type is being combined. Then the concentrations could be used in an appropriate titration calculation on the total heat values from box 604. The titration calculation obtains an equilibrium constant $K_d$ for the fragment type and this result can be saved in titration data 464.

The operation in box 606 can then use the saved $K_d$ values to obtain each fragment's ligand efficiency value. The relationship $LE \approx (RT(\ln K_d))/N$ can be used to obtain a ligand efficiency value LE from a $K_d$ value for each fragment type, with R being the gas constant, T the absolute temperature, and N the number of heavy atoms in the fragment type. The ligand efficiency values obtained in box 606 can then be saved in fragment ranking data 466. The operation in box 606 can save an ordered list of the fragment types, which can, for example, be a simple rank ordering made by comparing magnitudes of LE or other data indicating binding strength.

The operation in box 608 then provides a ranking of fragment types for the target type, such as through external I/O 416 or a user interface (not shown). The ranking can, for example, be a rank ordered list of fragment types as described above, optionally also including their ligand efficiencies and $K_d$ values. The ranking from box 608 can then be used in any appropriate way, such as in selecting compounds to be combined and/or modified using medicinal chemistry for possible testing as therapeutic or diagnostic agents—compounds could be chosen that include highly ranked fragment types. A ranked list of fragment types is, however, only one of various rankings that could be provided in box 608; it would also be possible, for example, to provide a fragment type's ligand efficiency value in real time, as it is obtained, or to provide ligand efficiencies for a number of fragment types in any other appropriate data structure rather than a rank ordered list.

The operations in boxes 606 and 608 can be repeated for a number of target types, as indicated by the dashed line from box 608 to box 606. In this case, each target type's ranking could be provided as output when obtained, or the rankings of a group of target types could instead be provided as output after all have been obtained.

A system as in FIGS. 6-10 could be implemented in many ways. In one successful prototype implementation, for example, a number of processors are included in processing components 402; also, digital temperature data, such as from lock-in amplifiers, are loaded into an external data base by a processor that performs measurement, allowing access by one or more other processors to perform data analysis. A production system, however, might have only one processor that performs both measurement and data analysis. Also, a prototype implementation has successfully performed closed loop environmental control, and it might prove feasible to make other operations fully automatic so that no human participation is required, such as in array positioning or sample deposition.

In one example, a prototype implementation has measured hsp90 with noise of approximately 0.5 J/L, averaging over five measurements. It is believed this can be improved by a factor of three by reducing extrinsic noise as described above, which is significantly higher than intrinsic noise because it can result from many different factors including several relating to injection of drops into sample and reference regions. Intrinsic noise from fluctuations in voltage signals from thermal sensors has been reduced to 0.05 J/L.

Many possible uses exist for fragment type rankings as obtained in FIGS. 1 and 6-10, and operations like those in FIGS. 7-10 could be implemented with a wide variety of existing technologies; rankings obtained by the techniques described above are useful in screening compounds for possible use, as in drug discovery by a pharmaceutical company. More specifically, the techniques of FIGS. 1-10 are useful in fragment-based screening (FBS). While previous high-throughput screening techniques use compound libraries of one to two million compounds with molecular weights of 300-500 Da, FBS techniques can be implemented with smaller libraries on the order of 1000 compounds, each with a lower molecular weight such as 150-250 Da. As described above, some FBS techniques perform screening at high concentrations using a biophysical technique such as X-ray crystallography or NMR. The techniques of FIGS. 1-10 can be implemented to obtain ligand efficiency information and other ranking information about fragments, information that cannot be obtained using X-ray analysis and is difficult to obtain with NMR.

Furthermore, the techniques described above can perform calorimetry on very small samples in very sensitive systems, making it possible to rank fragment types with small amounts of target material and fragment material and in a much shorter time than would be possible with larger scale techniques such as those typically referred to as "microcalorimetry." Larger scale techniques require more time, for example, because each sample requires more time to reach thermal equilibrium and each reaction takes more time because of long diffusion times. Also, in some larger scale techniques, a small drop of one reagent (e.g. 100-1000 nL) is dropped into a large reservoir of another reagent (e.g. 10 µL), leading to concentration issues that in turn lead to solvent matching issues. For example, if the small drop includes fragments, the concentration will be very high, requiring an undiluted or only slightly diluted DMSO solvent if using library compounds having concentrations of about 200 millimolar. But to prevent heat of mixing from high concentration of DMSO from swamping out temperature measurements, the target needs to be at the same concentration in the reservoir, causing it to precipitate out, precluding successful FBS.

Also, known commercial implementations of larger scale techniques do not employ very sensitive, low noise calorimeters as described above. One relatively sensitive system has published projected specifications with heat sensitivity less than 3 µJ, power sensitivity less than 50 nW, and baseline sensitivity less than 5 nW, leading to an estimated noise level of 0.15-0.3 J/L, but it is believed that significantly greater sensitivity can be achieved with the techniques described above. Some known commercial implementations also lack circuitry to eliminate common-mode components other than by measurement and subsequent subtraction.

The techniques of FIGS. 1-10 could be implemented to perform FBS in a complementary manner with X-ray crystallography and NMR techniques. For example, techniques as described above could be used to pre-screen compounds for X-ray crystallography, which may be particularly useful for situations in which there are no existing crystals of a free protein of interest. Fragment "hits," meaning types of fragments that have higher ligand efficiencies, could be used directly in co-crystallization trials and could be subjected to chemical optimization and retesting prior to use for co-crystallization. In general, the above techniques do not obtain structural information, which is available from X-ray crystallography or NMR techniques; it is possible, however, that the above techniques could be used in a competition assay to identify a ligand binding site.

Even though NMR techniques could be used in some cases to determine the equilibrium constant $K_d$, some NMR techniques have inherent protein size limitations, and the above techniques do not have such limitations. Where appropriate, the above techniques could be used for preliminary screening, NMR techniques could then be used for pre-screening, and finally X-ray crystallography could be performed on a reduced number of compounds selected based on the other techniques.

Some of the implementations as described above in relation to FIGS. 1-10 illustrate examples of a method of using array calorimeters. For each of a set of cells of an array calorimeter, the method provides respective test and reference groups of samples, with the test group including at least a first sample with molecules of one or more target types and a second sample with fragments of one or more fragment types; each of the first and second samples has a volume that does not exceed approximately 100 microliters. The reference group in each cell includes first and second samples similar to the test group's first and second samples. The method combines at least the first and second samples of the cell's test and reference groups, and the method also provides output signals that include information about heat of reaction due to combining the first and second samples of the cell's test group. Then, for each of a set of the target types, the method uses the output signals to rank fragment types that react with the target type.

In specific implementations, the first and second samples can have volumes that do not exceed approximately 10 microliters, approximately one microliter, approximately 500 nanoliters, or approximately 250 nanoliters. The use of output signals to rank fragment types can include at least one of the following: Identifying a subset of fragment types that react measurably with the target type; obtaining an equilibrium constant for each of a subset of the fragment types that react measurably with the target type; obtaining a ligand efficiency value for reach of a subset of the fragment types that react measurably with the target type; and obtaining a rank ordering of a subset of the fragment types that react measurably with the target type, such as a rank ordering that depends on ligand efficiencies.

In further specific implementations, the output signals can be electrical signals, including at least one of analog electrical signals and digital electrical signals. The first and second samples in each cell's test group can have dilution that is not greater than approximately 10:1. In each cell, the first and second samples of the test and reference groups can be combined concurrently.

In further specific implementations, for at least two of the cells, there can be an overlap in time between the cells' acts of providing test and reference groups, combining at least first and second samples, and providing output signals. The acts of providing test and reference groups can be performed for all the cells before beginning any of the cells' acts of combining samples and providing output signals. Also, after providing groups of samples for all the cells, the samples can be allowed to come to thermal equilibrium before beginning the acts of combining samples and providing output signals for any of the cells. Alternatively, the acts of providing samples, combining samples, and providing output signals can all be completed for a first cell before beginning those acts for a second cell.

In further specific implementations, each cell's output signals can include a signal component with information about heat of reaction and a noise component that can have a magnitude of approximately 1.0 Joules/Liter or less, or even a magnitude of approximately 0.3 Joules/Liter or less. Each cell can include test and reference regions in which the test and reference groups are combined, respectively, and the first and second samples of each test and reference group can be droplets; each cell's act of combining can include positioning the first and second samples of the test group and reference group in the test and reference regions, respectively, and electrostatically causing the first and second samples in each region to merge and mix. An extrinsic portion of the noise component can result during the acts of positioning the samples and electrostatically causing the samples to merge and mix. Each cell's act of providing output signals can include obtaining test and reference thermal signals and obtaining a difference signal indicating difference between the test and reference thermal signals; the test thermal signals can indicate heat of reaction from combining the test group's first and second samples while the reference thermal signal can indicate temperature resulting from combining the reference group's first and second samples, so that the difference signal can include the extrinsic portion of the noise component but not a common-mode component present in both the test and reference thermal signals. The reference group of samples, for example, can be samples that do not react with each other when combined. The extrinsic portion can result due to mixing and diffusion slower than the characteristic time for thermal dissipation, differences between test and reference sample volumes, sample shapes, sample temperatures, sample placements, reagent mixing, reagent diffusion, sample evaporation, convective or conductive heat transfer, or other violations of common mode.

In further specific implementations, an intrinsic portion of the noise component can result during the act of obtaining the difference signal. In obtaining the difference signal, the method can resistively sense the test and reference thermal signals and obtain analog signals indicating difference between the resistively sensed signals; the method can convert the analog signals to respective digital signals. The intrinsic portion can arise during the act of resistively sensing and obtaining analog signals and during the act of converting the analog signals. The intrinsic portion can be approximately 0.06 Joules/Liter or less.

In further specific implementations, the method, in using the output signals, can obtain an equilibrium constant $K_d$ for one of the fragment types that reacts with one of the target types, and can use $K_d$ to obtain data indicating ligand efficiency for the fragment type. The fragments of each fragment type in the test group's second sample can have a molecular weight not exceeding approximately 250 Da. The calorimeter can be a nanocalorimeter.

Some of the implementations in relation to FIGS. 1-10 also illustrate examples of a method of using array calorimeters that includes performing a series of one or more iterations, after which output signals from the series of iterations are used to rank fragment types that react with a target type. Each iteration can include, for a set of one or more cells of an array calorimeter, acts of providing test and reference groups of samples as described above, combining at least the first and second samples of the test and reference groups, and providing respective output signals that include information about heat of reaction due to combining the first and second samples of the test group.

In specific implementations, the same array calorimeter can be used in two or more of the iterations in the series. Also, in first and second iterations in the series, first and second array calorimeters can be used respectively.

Some of the implementations described above also illustrate examples of a method of using array calorimeters that includes performing a first series of one or more iterations and a second series of one or more iterations. Each iteration in the first series can include, for each of a set of cells, acts of providing test and reference groups of samples as described above, combining at least the first and second samples of the test and reference groups, and providing output signals as described above; the output signals from the first series of iterations can then be used to identify fragment types that react measurably with each of a set of one or more of the target types. Each iteration in the second series can similarly include providing test and reference groups of samples, combining at least the first and second samples, and providing respective output signals, with the target type in each cell's test group being one of those for which reacting fragment types are identified in the first series and with samples of the target type being provided to cells whose second samples include different concentrations of fragment types identified as reacting with the target type in the first series; the output signals from the second series of iterations can be used to rank fragment types according to ligand efficiency for one or more of the target types.

Some of the exemplary implementations described above in relation to FIGS. 1-10 also illustrate examples of a system that includes a calorimetric component, a sample providing component, and processing circuitry. The calorimetric component is structured to combine test and reference groups of samples in each of a number of regions, to obtain test thermal signals indicating heat of reaction for the combined test group and reference thermal signals indicating temperature of the combined reference group; in response to the test and reference thermal signals, the calorimetric component provides output signals that include information about the heat of reaction. The sample providing component is structured to provide samples to the regions. The processing circuitry is connected to control the calorimetric component and the sample providing component and to receive the output signals. The processing circuitry is programmed to control the sample providing component to provide test and reference groups of samples as described above, to control the calorimetric component to combine the test and reference groups of at least two of the regions, to receive output signals from the calorimetric component for two or more regions whose test and reference groups are combined, and to use the output signals to rank fragment types that react with each of one or more of the target types.

In a specific implementation, the calorimetric component includes a nanocalorimeter in which test and reference groups of two or more regions can be combined in parallel.

The techniques described above can make use of current technology to perform FBS with reduced material requirements and at high speed, to rank fragment types, such as by obtaining data indicating ligand efficiencies or other binding constants. It is foreseeable that sensitivity and speed of the techniques will continue to improve over time. At current system throughput, it is estimated that an initial screen of 384 fragment types would require less than 1.5 mg of protein, and it is foreseeable that an initial screen could be performed with less protein as techniques improve. Assuming a 10% hit rate, if one also determines the $K_d$ of each of the confirmed hits, the total protein requirement is less than 3 mg for initial screen, identification, and titrations. Improvements in speed are also foreseeable, for example, because smaller amounts of material can be deposited and mixed more quickly and because smaller integrated structures and computational advances will allow greater parallelism. The expected affinity of FBS hits lies in the range of greatest sensitivity for the system described above. As explained above, a $K_d$ value obtained using the above described techniques can in turn be used to obtain ligand efficiency for hits. As with conventional techniques, FBS performed as described above relies on automated or partially automated data collection and processing, and it is foreseeable that data collection and processing techniques will also improve.

The implementations in FIGS. 1-10 illustrate various techniques that are especially suitable for FBS. The techniques could be readily extended to other techniques that rank fragment types for small samples in low-noise calorimeters.

The exemplary implementations described above employ systems with particular nanocalorimeters and other components connected and operating in specific ways, but various other systems could be used, with different calorimeters or other devices for measuring heats of reaction and other components connected and operated differently than described above, and with various other shapes, dimensions, or other numerical or qualitative characteristics other than those illustrated and described above. For example, the thermistor materials described above include many that are currently known to be appropriate, but it is foreseeable that new thermistor materials will be developed, and also that new thermal sensing techniques will be developed; similarly, other types of drop mergers or other sample combining techniques could be used. Similarly, the signals described above are generally electrical signals, either analog or digital, but various other types of signals could be employed, including, for example, some types of mechanical signals. Also, specific types of processors and other system components, software, and data structures are mentioned above, but any processors with system components, software, and data structures could be used, including types hereafter developed. In addition, various nanocalorimeter dimensions could be used, as would be appropriate for different sample sizes or for different sample combining techniques, and various types of analog and digital output signals and other types of output signals could be used in various ways to rank fragment types in various ways.

The above exemplary implementations generally involve analysis of digital temperature values and other screening and analysis techniques following particular operations, but different operations could be performed, the order of the operations could be modified, and additional operations could be added within the scope of the invention. For example, some of the exemplary implementations perform intermediate calculations that obtain intermediate results, such as $K_d$ or ligand efficiency, for use in obtaining other results, and it is foreseeable that other implementations could obtain the same or similar results while omitting or modifying such intermediate calculations.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of using array calorimeters, comprising:
   for each of a set of two or more cells of an array calorimeter:
   providing respective test and reference groups of samples; the test group including at least a respective first sample that includes molecules of one or more target types and a respective second sample that includes fragments of one or more fragment types, each of the first and second samples not exceeding approximately 100 microliters; the reference group including respective first and second samples similar to the test group's first and second samples;
   combining at least the first and second samples of the cell's test and reference groups; and
   providing respective output signals that include information about heat of reaction due to combining the first and second samples of the cell's test group; and
   for each of a set of one or more of the target types, using the output signals to rank fragment types that react with the target type; the act of using the output signals to rank fragment types including at least one of:
   identifying a subset of the fragment types that react measurably with the target type;
   obtaining an equilibrium constant for each of a subset of the fragment types that react measurably with the target type;
   obtaining a ligand efficiency value for each of a subset of the fragment types that react measurably with the target type; and
   obtaining a rank ordering of a subset of the fragment types that react measurably with the target type, the rank ordering depending on ligand efficiencies of the fragment types.

2. The method of claim 1 in which each of the first and second samples do not exceed approximately 10 microliters, approximately one microliter, approximately 500 nanoliters, or approximately 250 nanoliters.

3. The method of claim 2 in which each of the first and second samples do not exceed approximately 250 nanoliters.

4. The method of claim 1 in which the output signals are electrical signals.

5. The method of claim 4 in which the output signals include at least one of analog electrical signals and digital electrical signals.

6. The method of claim 1 in which each of the first and second samples in each cell's test group has no greater than approximately 10:1 dilution.

7. The method of claim 1 in which, in each cell's act of combining, the first and second samples of the cell's test and reference groups are combined concurrently.

8. The method of claim 1 in which, for at least two of the cells in the set, there is an overlap in time between the cells' respective acts of providing test and reference groups of samples, combining at least the first and second samples, and providing output signals.

9. The method of claim 8 in which the cells' respective acts of providing test and reference groups of samples are all performed before beginning any of the cells' respective acts of combining at least the first and second samples and providing output signals.

10. The method of claim 9, further comprising:
after the cells' respective acts of providing test and reference groups of samples are all performed, allowing the first and second samples to come to thermal equilibrium before beginning any of the cells' respective acts of combining at least the first and second samples and providing output signals.

11. The method of claim 1 in which, for first and second cells in the set, the first cell's respective acts of providing test and reference groups of samples, combining at least the first and second samples, and providing output signals are completed before beginning the second cell's respective acts of providing test and reference groups of samples, combining at least the first and second samples, and providing output signals.

12. The method of claim 1 in which each cell's output signals include a respective signal component with information about respective heat of reaction and a respective noise component with a magnitude of approximately 1.0 Joules/Liter or less.

13. The method of claim 12 in which the noise component has a magnitude of approximately 0.3 Joules/Liter or less.

14. The method of claim 12 in which each cell includes respective test and reference regions in which the cell's test and reference groups are combined, respectively; the first and second samples of each test and reference group being droplets; each cell's act of combining at least the first and second samples comprising:
positioning the first and second samples of a cell's test group and reference group in the cell's test and reference regions, respectively; and
electrostatically causing the first and second samples in the cell's test and reference regions to merge and mix;
an extrinsic portion of the respective noise component resulting during the acts of positioning the first and second samples and electrostatically causing the first and second samples to merge and mix.

15. The method of claim 14 in which each cell's act of providing output signals comprises:
obtaining test and reference thermal signals, the test thermal signal indicating heat of reaction resulting from combining the test group's first and second samples, the reference thermal signal indicating temperature resulting from combining the reference group's first and second samples; and
obtaining a difference signal indicating difference between the test and reference thermal signals; the difference signal including the extrinsic portion of the noise component but not including a common-mode component present in both the test and reference thermal signals.

16. The method of claim 15 in which the reference group of samples do not react with each other when combined.

17. The method of claim 15 in which the extrinsic portion results due to one or more of mixing and diffusion slower than the characteristic time for thermal dissipation, differences between test and reference sample volumes, sample shapes, sample temperatures, sample placements, reagent mixing, reagent diffusion, sample evaporation, convective or conductive heat transfer, or other violations of common mode.

18. The method of claim 15 in which an intrinsic portion of the noise component results during the act of obtaining the difference signal.

19. The method of claim 18 in which the act of obtaining the difference signal comprises:
resistively sensing the test and reference thermal signals and obtaining analog signals indicating difference between the resistively sensed test and reference thermal signals; and
converting the analog signals to respective digital signals;
the intrinsic portion arising during the act of resistively sensing and obtaining analog signals and during the act of converting the analog signals.

20. The method of claim 18 in which the intrinsic portion is approximately 0.05 Joules/Liter or less.

21. The method of claim 1 in which the act of using the output signals further includes:
for one fragment type that reacts with one of the target types in the set, obtaining an equilibrium constant $K_d$; and
using $K_d$ to obtain data indicating ligand efficiency for the fragment type.

22. The method of claim 1 in which fragments of each fragment type in the test group's second sample for each cell have a molecular weight not exceeding approximately 250 Da.

23. The method of claim 1 in which the calorimeter is a nanocalorimeter.

24. The method of claim 1 in which the method is performed using a system that includes the array calorimeter;
the array calorimeter being structured to combine respective test and reference groups of samples in each of a number of regions, to obtain respective test thermal signals indicating respective heat of reaction for each region's combined test group and respective reference thermal signals indicating temperature of each region's combined reference group, and, in response to region's test and reference thermal signals, to provide respective output signals that include information about the heat of reaction due to combining the region's test group;
the system further including:
a sample providing component structured to provide samples to the regions; and
processing circuitry connected to control the calorimetric component and the sample providing component and connected to receive the output signals; the processing circuitry being programmed to perform the acts of providing the test and reference groups of samples, combining at least the first and second samples, and providing output signals by:
controlling the sample providing component to provide respective test and reference groups of samples to a set of at least two of the regions; a set of two or more of the test groups including a first sample that includes molecules of one or more target types and a second sample that includes fragments of one or more fragment types, each of the first and second samples not exceeding approximately 100 microliters;
controlling the calorimetric component to combine the test and reference groups of at least two of the regions in the set;
receiving output signals from the calorimetric component for two or more of the regions whose test and reference groups are combined; and for each of a set of one or more of the target types, using the output signals to rank fragment types that react with the target type.

25. The method of claim 24 in which the calorimetric component includes a nanocalorimeter in which test and reference groups of two or more regions can be combined in parallel.

26. A method of using array calorimeters, comprising:
performing a series of one or more iterations, each iteration including, for each of a respective set of one or more cells of an array calorimeter that includes two or more cells:
providing a test group of samples and a reference group of samples; the test group including at least a respective first sample that includes molecules of one or more target types and a respective second sample that includes fragments of one or more fragment types, each of the first and second samples not exceeding approximately 100 microliters; the reference group including respective first and second samples similar to the test group's first and second samples;
combining at least the first and second samples of the cell's test and reference groups; and
providing respective output signals that include information about heat of reaction due to combining the first and second samples of the cell's test group; and
for each of a set of one or more of the target types, using the output signals from the series of iterations to rank fragment types that react with the target type; the act of using the output signals to rank fragment types including at least one of:
identifying a subset of the fragment types that react measurably with the target type;
obtaining an equilibrium constant for each of a subset of the fragment types that react measurably with the target type;
obtaining a ligand efficiency value for each of a subset of the fragment types that react measurably with the target type; and
obtaining a rank ordering of a subset of the fragment types that react measurably with the target type, the rank ordering depending on ligand efficiencies of the fragment types.

27. The method of claim 26 in which the same array calorimeter is used in two or more of the iterations in the series.

28. The method of claim 26 in which, in first and second iterations in the series, first and second array calorimeters are used respectively.

29. A method of using array calorimeters, comprising:
performing a first series of one or more iterations, each iteration in the first series including, for each of a respective set of one or more cells of an array calorimeter:
providing a test group of samples and a reference group of samples; the test group including at least a respective first sample that includes molecules of one or more target types and a respective second sample that includes fragments of one or more fragment types, each of the first and second samples not exceeding approximately 100 microliters; the reference group including respective first and second samples similar to the test group's first and second samples;
combining at least the first and second samples of the cell's test and reference groups; and
providing respective output signals that include information about heat of reaction due to combining the first and second samples of the cell's test group; and
for each of a set of one or more of the target types, using the output signals from the first series of iterations to identify fragment types that react measurably with the target type;
performing a second series of one or more iterations, each iteration in the second series including, for each of a respective set of one or more cells of an array calorimeter:
providing a test group of samples and a reference group of samples; the test group including at least a respective first sample that includes molecules of a respective target type in a subset of one or more of the target types in the set and a respective second sample that includes fragments of a respective fragment type identified in the first series of iterations as reacting measurably with the respective target type, each of the first and second samples not exceeding approximately 100 microliters; the reference group including respective first and second samples similar to the test group's first and second samples; for each target type in the subset, first samples that include molecules of the target type being provided to a number of cells whose second samples include different concentrations of fragment types identified as reacting measurably with the target type;
combining at least the first and second samples of the cell's test and reference groups; and
providing respective output signals that include information about heat of reaction due to combining the first and second samples of the cell's test group; and
for at least one or more of the target types in the subset, using the output signals from the second series of iterations to rank fragment types identified as reacting measurably with the target type according to ligand efficiency.

30. The method of claim 29 in which the act of using the output signals from the second series of iterations to rank fragment types includes at least one of:
analyzing heat of reaction as a function of fragment concentration for each of a subset of the fragment types that react measurably with the target type;
obtaining an equilibrium constant for each of a subset of the fragment types that react measurably with the target type;
obtaining a ligand efficiency value for each of a subset of the fragment types that react measurably with the target type; and
obtaining a rank ordering of a subset of the fragment types that react measurably with the target type, the rank ordering depending on ligand efficiencies of the fragment types.

31. A method of using array calorimeters, comprising:
for each of a set of two or more cells of an array calorimeter:
providing respective test and reference groups of samples; the test group including at least a respective first sample that includes molecules of one or more target types and a respective second sample that includes fragments of one or more fragment types, each of the first and second samples not exceeding approximately 100 microliters; the reference group including respective first and second samples similar to the test group's first and second samples;
combining at least the first and second samples of the cell's test and reference groups; and providing respective output signals that include information about enthalpy released due to combining the first and second samples of the cell's test group; and for each of a set of one or more of the target types, using the output signals to rank fragment types that react with the target type; the act of using the output signals to rank fragment types including:

analyzing enthalpy released as a function of fragment concentration for each of a subset of the fragment types that react with the target type.

32. The method of claim 31 in which the act of analyzing enthalpy includes at least one of:

obtaining an equilibrium constant for each of the subset of the fragment types;

obtaining a ligand efficiency value for each of the subset of the fragment types; and obtaining a rank ordering of the subset of the fragment types, the rank ordering depending on ligand efficiencies of the fragment types.

* * * * *